US007329541B2

(12) United States Patent
Barbas

(10) Patent No.: US 7,329,541 B2
(45) Date of Patent: Feb. 12, 2008

(54) ZINC FINGER BINDING DOMAINS FOR GNN

(75) Inventor: Carlos F. Barbas, Solana Beach, CA (US)

(73) Assignee: The Scripps Research Institute, La Jolla, CA (US)

(*) Notice: Subject to any disclaimer, the term of this patent is extended or adjusted under 35 U.S.C. 154(b) by 21 days.

(21) Appl. No.: 11/351,561

(22) Filed: Feb. 10, 2006

(65) Prior Publication Data

US 2006/0223757 A1 Oct. 5, 2006

Related U.S. Application Data

(60) Division of application No. 10/646,919, filed on Aug. 21, 2003, now Pat. No. 7,101,972, which is a continuation of application No. 09/494,190, filed on Jan. 28, 2000, now Pat. No. 6,610,512, which is a continuation-in-part of application No. PCT/EP99/07742, filed on Oct. 14, 1999, which is a continuation-in-part of application No. 09/173,941, filed on Oct. 16, 1998, now Pat. No. 6,140,081.

(51) Int. Cl.
C07H 17/00 (2006.01)
C07K 14/00 (2006.01)

(52) U.S. Cl. ............... 435/320.1; 536/23.1; 530/350; 514/2

(58) Field of Classification Search .......... 530/350; 536/23.1; 435/320.1; 514/2
See application file for complete search history.

(56) References Cited

U.S. PATENT DOCUMENTS

| 5,223,409 A | 6/1993 | Ladner et al. |
| 5,789,538 A | 8/1998 | Rebar et al. |
| 2002/0081614 A1 | 6/2002 | Case et al. |

FOREIGN PATENT DOCUMENTS

| WO | WO91/07509 | 5/1991 |
| WO | WO95/19431 | 7/1995 |
| WO | WO96/06166 | 2/1996 |
| WO | WO 00/23464 | 4/2000 |

OTHER PUBLICATIONS

J.Miller et al., "Repetitive Zinc-Binding Domains in the Protein Transcription Factor IIIA from Xenopus Oocytes," EMBO J. 4: 1609-1614 (1985).
I. Sadowski et al., "GAL4-VP16 is an Unusually Potent Transcriptional Activator," Nature355:563-564 (1988).
M.S. Lee et al., "Three-Dimensional Solution Structure of a Single Zinc Finger DNA-Binding Domain," Science 245: 635-637 (1989).

(Continued)

*Primary Examiner*—Karen Cochrane Carlson
(74) *Attorney, Agent, or Firm*—Catalyst Law Group, APC; Michael B. Farber, Esq.

(57) ABSTRACT

Zinc finger-nucleotide binding polypeptides having binding specificity for target nucleotides containing one or GNN triplets are provided. Compositions containing such polypeptides and the use of such polypeptides and compositions for regulating gene expression are also provided.

18 Claims, 7 Drawing Sheets

| Target 5'---3' (SEQ ID NO:) | Binding-helix amino acids at positions -1 1 2 3 4 5 6 | Specificity |
|---|---|---|
| GAA (1) | Q S S N L V R | GAA (GAT) |
| (17) | Q R S N L V R | GAA, GAT |
| (18) | Q S G N L V R | GAN |
| (19) | Q P G N L V R | GAN |
| GAC (2) | D P G N L V R | GAC |
| (20) | D P G N L K R | GAC, GAT |
| GAG (3) | R S D N L V R | GAG |
| (21) | R S D N L R R | GAG, GGG |
| (22) | K S A N L V R | GAG, (GAT) |
| (23) | R S D N L V K | GAG, (GGG) |
| (24) | K S A Q L V R | UNSPEC. |
| GAT (4) | T S G N L V R | GAT |
| GCA (5) | Q S G D L R R | GCA, GCT |
| (25) | Q S S T L V R | GTA, GCA |
| (26) | Q S G T L R R | GTA, GCA/T/C |
| (27) | Q P G D L V R | GCT, GCC, GCA |

OTHER PUBLICATIONS

N.P. Pavletich & C.O. Pabo, "Zinc Finger-DNA Recognition: Crystal Structure of a Zif268-DNA Complex at 2.1 A," Science 252: 809-817 (1991).

C.F. Barbas III et al., "Assembly of Combinatorial Antibody Libraries on Phage Surfaces: The Gene III Site," Proc. Natl. Acad. Sci. USA 88: 7978-7982 (1991).

N.P. Pavletich & C.O. Pabo, "Crystal Structure of a Five-Finger GLI-DNA Complex: New Perspectives on Zinc Fingers," Science 261: 1701-1707 (1993).

E.J. Rebar & C.O. Pabo, "Zinc Finger Phage: Affinity Selection of Fingers with New DNA-Binding Specificities," Science 263: 671-673 (1994).

H. Wu et al., "Building Zinc Fingers by Selection: Toward a Therapeutic Application," Proc. Natl. Acad. Sci. USA 92: 344-348 (1995).

M. Elrod-Erickson et al., "Zif268 Protein-DNA Complex Refined at 1.6 Å: A Model System for Understanding Zinc Finger-DNA Interactions," Structure 4: 1171-1180 (1996).

C.A. Kim et al., "A 2.2 Å Resolution Crystal Structure of a Designed Zinc Finger Protein Bound to DNA," Nature Struct. Biol. 3: 940-945 (1996).

H.A. Greisman & C.O. Pabo, "A General Strategy for Selecting High-Affinity Zinc Finger Proteins for Diverse DNA Target Sites," Science 275: 657-661 (1997).

J.-S. Kim et al., "Design of TATA Box-Binding Protein/Zinc Finger Fusions for Targeted Regulation of Gene Expression," Proc. Natl. Acad. Sci. USA 94: 3616-3620 (1997).

Q. Liu et al., "Design of Polydactyl Zinc-Finger Proteins for Unique Addressing within Complex Genomes," Proc. Natl. Acad. Sci. USA 94: 5525-5530 (1997).

C. Rader & C.F. Barbas III, "Phage Display of Combinatorial Antibody Libraries," Curr. Opin. Biotechnology 8: 503-508 (1997).

J.S. Kim & C.O. Pabo, "Transcriptional Repression by Zinc Finger Peptides," J. Biol. Chem. 272: 29795-29800 (1997).

M. Eilrod-Erickson et al., "High-Resolution Structures of Variant Zif268-DNA Complexes: Implications for Understanding Zinc Finger . . . ," Structure 6: 451-464 (1998).

R.R. Beerli et al., "Toward Controlling Gene Expression at Will: Specific Regulation of the erbB-2/HER-2 Promoter by . . . ,"Proc. Natl. Acad. Sci. USA 95: 14628-14633 (1998).

D.J. Segal et al., "Toward Controlling Gene Expression at Will: Selection and Design of Zinc Finger Domains Recognizing . . . ," Proc. Natl. Acad. Sci. USA 96: 2758-2763 (1999).

B. Gebelein et al., "A Novel Profile of Expressed Sequence Tags for Zinc Finger Encoding Genes from the Poorly Differentiated . . . ,"Cancer Lett. 105: 225-231 (1996).

T. Ogawa et al., "Enhanced Expression in Seminoma of Human Zinc Finger Genes Located on Chromosome 19," Cancer Genet. Cytogenet. 100: 36-42 (1998).

Y.Choo & A. Klug, "Selection of DNA Binding Sites for Zinc Fingers Using Rationally Randomized DNA . . . ," Proc. Natl. Acad. Sci. USA 91: 11168-11172 (1994).

Y. Choo & A. Klug, "Toward a Code for the Interactions of Zinc Fingers with DNA: Selection of Randomized Fingers . . . ," Proc. Natl. Acad. Sci. USA 91: 11163-11167 (1994).

Fig. 1

| Target 5'---3' (SEQ ID NO:) | Binding-helix amino acids at positions -1 1 2 3 4 5 6 | Specificity |
|---|---|---|
| GAA (1) | Q S S N L V R | GAA (GAT) |
| (17) | Q R S N L V R | GAA, GAT |
| (18) | Q S G N L V R | GAN |
| (19) | Q P G N L V R | GAN |
|  |  |  |
| GAC (2) | D P G N L V R | GAC |
| (20) | D P G N L K R | GAC, GAT |
|  |  |  |
| GAG (3) | R S D N L V R | GAG |
| (21) | R S D N L R R | GAG, GGG |
| (22) | K S A N L V R | GAG, (GAT) |
| (23) | R S D N L V K | GAG, (GGG) |
| (24) | K S A Q L V R | UNSPEC. |
|  |  |  |
| GAT (4) | T S G N L V R | GAT |
|  |  |  |
| GCA (5) | Q S G D L R R | GCA, GCT |
| (25) | Q S S T L V R | GTA, GCA |
| (26) | Q S G T L R R | GTA, GCA/T/C |
| (27) | Q P G D L V R | GCT, GCC, GCA |

Fig. 1 (Cont.)

|  | | | |
|---|---|---|---|
|  | (28) | Q G P D L V R | GCT, GCA |
|  | (29) | Q A G T L M R | GTA, GCA |
|  | (30) | Q P G T L V R | GTA, GCA |
|  | (31) | Q G P E L V R | non-binder |
| GCC | (6) | D C R D L A R | GCC |
|  | (32) | G C R E L S R | GCC |
|  | (33) | D P S T L K R | GCC (GCA/T GTC) |
|  | (34) | D P S D L K R | GCC, GAC |
|  | (35) | D S G D L V R | GCC, GAC |
|  | (36) | D S G E L V R | GCT, GCC |
|  | (37) | D S G E L K R | GCT, GCC, GTC |
| GCG | (7) | R S D D L V K | GCG |
|  | (38) | R L D T L G R | GNG |
|  | (39) | R P G D L V R | GCG, GNG, GCN |
|  | (40) | R S D T L V R | NG |
|  | (41) | K S A D L K R | GAG, GTG, GCT, GCC |
|  | (42) | R S D D L V R | GAG, (GNG, GCN) |
|  | (43) | R S D T L V K | GNG |

Fig. 1 (Cont.)

|     | |     |     |
|-----|-----|-----|-----|
|     | (44) | K S A E L K R | GCT, GCC, UNSPEC. |
|     | (45) | K S A E L V R | GCT, GCC, UNSPEC. |
|     | (46) | R G P E L V R | UNSPEC. |
|     | (47) | K P G E L V R | NON-BINDER, BUT EXPR. |
|     |     |     |     |
| GCT | (8) | T S G E L V R | GCT |
|     | (48) | S S Q T L T R | GCT |
|     | (49) | T P G E L V R | GCT |
|     | (50) | T S G D L V R | GCT, (GCC, GCA) |
|     | (51) | S S Q T L V R | GCT |
|     | (52) | T S Q T L T R | GCT (GAT, GTC, GCC) |
|     | (53) | T S G E L K R | GCT, GCC |
|     | (54) | Q S S D L V R | GCT (GCA, GCC) |
|     | (55) | S S G T L V R | GCC, GCT |
|     | (56) | T P G T L V R | GCT, GTC |
|     | (57) | T S Q D L K R | GCC, GCT |
|     | (58) | T S G T L V R | GCT, UNSPEC. |
|     |     |     |     |
| GGA | (9) | Q R A H L E R | GGA |
|     | (59) | Q S S H L V R | GGA |
|     | (60) | Q S G H L V R | GGA |

Fig. 1 (Cont.)

|     |      |             |              |
|-----|------|-------------|--------------|
|     | (61) | Q P G H L V R | GGA, GCT   |
|     |      |             |              |
| GGC | (10) | D P G H L V R | GGC        |
|     | (62) | E R S K L A R | GGC        |
|     | (63) | D P G H L A R | GGC        |
|     | (64) | Q R A K L E R | GGC        |
|     | (65) | Q S S K L V R | GGC        |
|     | (66) | D R S K L A R | GGC, GGN   |
|     | (67) | D P G K L A R | GGC, unspec. |
|     |      |             |              |
| GGG | (11) | R S D K L V R | GGG        |
|     | (68) | R S D K L T R | GGG        |
|     | (69) | R S D H L T R | GGG, GAG   |
|     | (70) | K S A K L E R | NON-BINDER |
|     |      |             |              |
| GGT | (12) | T S G H L V R | GGT, GGA   |
|     | (71) | T A D H L S R | GGT, GAT   |
|     | (72) | T A D K L S R | GGG, (GGT) |
|     | (73) | T P G H L V R | GGT, unspec. |
|     | (74) | T S S H L V R | unspec.    |
|     | (75) | T S G K L V R | unspec.    |
|     |      |             |              |
| GTA | (13) | Q S S S L V R |            |
|     | (76) | Q P G E L V R | GTA, (GCT) |
|     | (77) | Q S G E L V R | GTA, GCA/C |

Fig. 1 (Cont.)

|     | (78) | Q S G E L R R | GTA, GCA/T/C |
|-----|------|---------------|--------------|
| GTC | (14) | D P G A L V R |              |
|     | (79) | D P G S L V R | GTC (GCT, GCC) |
| GTG | (15) | R S D E L V R | GTG, (GAG, GCG) |
|     | (80) | R K D S L V R | GTG, GNG     |
|     | (81) | R S D V L V R | GTG, GAG, GGG |
|     | (82) | R H D S L L R | GTG, GAG, GNG |
|     | (83) | R S D A L V R | GAG, GTG, GGG |
|     | (84) | R S S L V R   | GTG          |
|     | (85) | R S S H V R   | GTG, GGG     |
|     | (86) | R S D E L V K | GTG          |
|     | (87) | R S D A L V K | GAG GTG GGG  |
|     | (88) | R S D V L V K | GAG GNG      |
|     | (89) | R S S A L V R | GNG          |
|     | (90) | R K D S L V K | GGG GNG      |
|     | (91) | R S A S L V R | GAG, unspec. |
|     | (92) | R S D S L V R | GCT unspec.  |
|     | (93) | R I H S L V R | unspec.      |

Fig. 1(Cont.)

|     |       |             |                      |
|-----|-------|-------------|----------------------|
|     | (94)  | R P G S L V R | UNSPEC.            |
|     | (95)  | R G P S L V R | UNSPEC.            |
|     | (96)  | R P G A L V R | UNSPEC.            |
|     | (97)  | K S A S L V R | NON-BINDER         |
|     | (98)  | K S A A L V R | NON-BINDER         |
|     | (99)  | K S A V L V R | NON-BINDER         |
|     |       |             |                      |
|     |       |             |                      |
| GTT | (16)  | T S G S L V R | GTT, GCT          |
|     | (100) | T S G S L T R | GGT, GCT          |
|     | (101) | T S Q S L V R | GAT, GTA, GCT, GCA |
|     | (102) | T S S S L V R | GTA, GAT          |
|     | (103) | T P G S L V R | GTA               |
|     | (104) | T S G A L V R | GGT, GCT, GAT     |
|     | (105) | T P G A L V R | GGT, GAT, GCT     |
|     | (106) | T G G S L V R | GGT, GAT          |
|     | (107) | T S G E L V R | GCT GCG GTA GTT   |
|     | (108) | T S G E L T R | GCT GTA/T/C       |
|     | (109) | T S S A L V K | UNSPEC            |
|     | (110) | T S S A L V R | UNSPEC            |

```
        -30              erbB-2                  -1
        AGCCAT GGGGCCGGAGCCGCAGTG AGCACC       SEQ ID NO: 123

GCAATC GGAGCCGGAGCCGGAGTC CGGGGA       SEQ ID NO: 124
        -135             erbB-3                 -164
```

B

```
              10          20          30          40
E2C   MAQAALEPGEKPYACPECGKSF SRKDSLVR HQRTHTGEKP
E3    MAQAALEPGEKPYACPECGKSF SDPGALVR HQRTHTGEKP 50          60          70          80
E2C   YKCPECGKSF QSGDLRR HQRTHTGEKPYKCPECGKSF SD
E3    YKCPECGKSF QSSHLVR HQRTHTGEKPYKCPECGKSF SD 90         100         110         120
E2C   CRDLAR HQRTHTGEKPYACPECGKSF SQSSHLVR HQRTHT
E3    CRDLAR HQRTHTGEKPYACPECGKSF SQSSHLVR HQRTHT 130         140         150         160
E2C   GEKPYKCPECGKSF SDCRDLAR HQRTHTGEKPYKCPECGK
E3    GEKPYKCPECGKSF SDCRDLAR HQRTHTGEKPYKCPECGK 170         180
E2C   SF SRSDKLVR HQRTHTGKKTSGQAG        SEQ ID NO: 125
E3    SF SQSSHLVR HQRTHTGKKTSGQAG        SEQ ID NO: 126
```

ZINC FINGER BINDING DOMAINS FOR GNN

CROSS-REFERENCES

This application is a divisional application of U.S. patent application Ser. No. 10/646,919 by Barbas, filed on Aug. 21, 2003, now U.S. Pat. No. 7,101,972, which is a continuation of application Ser. No. 09/494,190, filed on Jan. 28, 2000, now U.S. Pat. No. 6,610,512, which is a continuation-in-part of PCT patent application Serial No. PCT/EP99/07742, filed on Oct. 14, 1999, which is a continuation-in-part of application Ser. No. 09/173,941, filed on Oct. 16, 1998, now U.S. Pat. No. 6,140,081.

STATEMENT REGARDING FEDERALLY SPONSORED RESEARCH AND DEVELOPMENT

This invention was made with U.S. government support under Contract No. GM 53910 by the National Institutes of Health. The government has certain rights in this invention.

TECHNICAL FIELD OF THE INVENTION

The field of this invention is zinc finger protein binding to target nucleotides. More particularly, the present invention pertains to amino acid residue sequences within the α-helical domain of zinc fingers that specifically bind to target nucleotides of the formula 5'-(GNN)-3'.

BACKGROUND OF THE INVENTION

The paradigm that the primary mechanism for governing the expression of genes involves protein switches that bind DNA in a sequence specific manner was established in 1967 (Ptashne, M. (1967) Nature (London) 214, 323-4). Diverse structural families of DNA binding proteins have been described. Despite a wealth of structural diversity, the $Cys_2$-$His_2$ zinc finger motif constitutes the most frequently utilized nucleic acid binding motif in eukaryotes. This observation is as true for yeast as it is for man. The $Cys_2$-$His_2$ zinc finger motif, identified first in the DNA and RNA binding transcription factor TFIIIA (Miller, J., McLachlan, A. D. & Klug, A. (1985) Embo J 4, 1609-14), is perhaps the ideal structural scaffold on which a sequence specific protein might be constructed. A single zinc finger domain consists of approximately 30 amino acids with a simple tua fold stabilized by hydrophobic interactions and the chelation of a single zinc ion (Miller, J., McLachlan, A. D. & Klug, A. (1985) Embo J 4,1609-14, Lee, M. S., Gippert, G. P., Soman, K. V., Case, D. A. & Wright, P. E. (1989) Science 245, 635-7). Presentation of the .alpha.-helix of this domain into the major groove of DNA allows for sequence specific base contacts. Each zinc finger domain typically recognizes three base pairs of DNA (Pavietich, N. P. & Pabo, C. O. (1991) Science (Washington, D.C., 1883-) 252, 809-17, Elrod-Erickson, M., Rould, M. A., Nekludova, L. & Pabo, C. O. (1996) Structure (London) 4, 1171-1180, Elrod-Erickson, M., Benson, T. E. & Pabo, C. O. (1998) Structure (London) 6, 451464, Kim, C. A. & Berg, J. M. (1996) Nature Structural Biology 3, 940-945), though variation in helical presentation can allow for recognition of a more extended site (Pavletich, N. P. & Pabo, C. O. (1993) Science (Washington, D.C., 1883-) 261, 1701-7, Houbaviy, H. B., Usheva, A., Shenk, T. & Burley, S. K. (1996) Proc Natl Acad Sci USA 93,13577-82, Fairall, L., Schwabe, J. W. R., Chapman, L., Finch, J. T. & Rhodes, D. (1993) Nature (London) 366, 483-7, Wuttke, D. S., Foster, M. P., Case, D. A., Goftesfeld, J. M. & Wright, P. E. (1997) J. Mol. Biol. 273, 183-206). In contrast to most transcription factors that rely on dimerization of protein domains for extending protein-DNA contacts to longer DNA sequences or addresses, simple covalent tandem repeats of the zinc finger domain allow for the recognition of longer asymmetric sequences of DNA by this motif. We have recently described polydactyl zinc finger proteins that contain 6 zinc finger domains and bind 18 base pairs of contiguous DNA sequence (Liu, Q., Segal, D. J., Ghiara, J. B. & Barbas III, C. F. (1997) PNAS 94, 5525-5530). Recognition of 18 bps of DNA is sufficient to describe a unique DNA address within all known genomes, a requirement for using polydactyl proteins as highly specific gene switches. Indeed, control of both gene activation and repression has been shown using these polydactyl proteins in a model system (Liu, Q., Segal, D. J., Ghiara, J. B. & Barbas III, C. F. (1997) PNAS 94,5525-5530).

Since each zinc finger domain typically binds three base pairs of sequence, a complete recognition alphabet requires the characterization of 64 domains. Existing information which could guide the construction of these domains has come from three types of studies: structure determination (Pavietich, N. P. & Pabo, C. O. (1991) Science (Washington, D.C., 1883) 252, 809-17, Elrod-Erickson, M., Rould, M. A., Nekludova, L. & Pabo, C. O. (1996) Structure (London) 4,1171-1180, Elrod-Erickson, M., Benson, T. E. & Pabo, C. O. (1998) Structure (London) 6, 451-464, Kim, C. A. & Berg, J. M. (1996) Nature Structural Biology 3, 940-945, Pavletich, N. P. & Pabo, C. O. (1993) Science (Washington, D.C., 1883-) 261, 1701-7, Houbaviy, H. B., Usheva, A., Shenk, T. & Burley, S. K. (1996) Proc Natl Acad Sci U.S.A. 93,13577-82, Fairall, L., Schwabe, J. W. R., Chapman, L., Finch, J. T. & Rhodes, D. (1993) Nature (London) 366, 483-7.,1 1, Wuttke, D. S., Foster,. M. P., Case, D. A., Gottesfeld, J. M. & Wright, P. E. (1997) J. Mol. Biol. 273, 183-206., Nolte, R. T., Conlin, R. M., Harrison, S. C. & Brown, R. S. (1998) Proc. Natl. Acad. Sci. U.S.A. 95,2938-2943, Narayan, V. A., Kriwacki, R. W. & Caradonna, J. P. (1997) J. Biol. Chem. 272, 7801-7809., site-directed mutagenesis (Isalan, M., Choo, Y. & Klug, A. (1997) Proc. Natl. Acad. Sci. U. S. A. 94, 5617-5621, Nardelli, J., Gibson, T. J., Vesque, C. & Charnay, P. (1991) Nature 349, 175-178, Nardelli, J., Gibson, T. & Charnay, P. (1992) Nucleic Acids Res. 20, 413744, Taylor, W. E., Suruki, H. K., Lin, A. H. T., Naraghi-Arani, P., Igarashi, R. Y., Younessian, M., Katkus, P. & Vo, N. V. (1995) Biochemistry 34, 3222-3230, Desjarlais, J. R. & Berg, J. M. (1992) Proteins: Struct., Funct., Genet. 12, 1014, Desjarlais, J. R. & Berg, J. M. (1992) Proc Natl Acad Sci USA 89, 7345-9), and phage-display selections (Choo, Y. & Klug, A. (1994) Proc Natl Acad Sci USA 91, 11163-7, Greisman, H. A. & Pabo, C. O. (1997) Science (Washington, D.C.) 275,657-661.23, Rebar, E. J. & Pabo, C. O. (1994) Science (Washington, D.C., 1883-) 263, 671-3, Jamieson, A. C., Kim, S.-H. & Wells, J. A. (1994) Biochemistry 33, 5689-5695, Jamieson, A. C., Wang, H. & Kim, S.-H. (1996) PNAS 93, 12834-12839, Isalan, M., Klug, A. & Choo, Y. (1998) Biochemistry 37, 12026-33, Wu, H., Yang, W.-P. & Barbas III, C. F. (1995) PNAS 92, 344-348). All have contributed significantly to our understanding of zinc finger/DNA recognition, but each has its limitations. Structural studies have identified a diverse spectrum of protein/DNA interactions but do not explain if alternative interactions might be more optimal. Further, while interactions that allow for sequence specific recognition are observed, little information is provided on how alternate sequences are excluded from binding. These questions have been partially addressed by mutagenesis of existing proteins, but the data is always limited by the number of mutants that can be characterized. Phage-display and selection of randomized libraries overcomes certain numerical limitations, but providing the appropriate selective pressure to ensure that both specificity and affinity drive the selection is difficult. Experimental studies from several laboratories (Choo, Y. & Klug, A. (1994) Proc Natl Acad Sci USA 91, 11163-7, Greisman, H. A. & Pabo, C. O. (1997) Science (Washington, D.C.) 275, 657-661, Rebar, E. J. & Pabo, C. O. (1994) Science (Washington, D.C., 1883-) 263, 671-3, Jamieson, A. C., Kim, S.-H. & Wells, J. A. (1994) Biochemistry 33, 5689-5695.25, Jamieson, A. C., Wang, H. & Kim, S.-H. (1996) PNAS 93, 12834-12839, Isalan, M., Klug, A. & Choo, Y. (1998) Biochemistry 37,12026-33), including our own (Wu, H., Yang, W.-P. & Barbas III, C. F. (1995) PNAS 92, 344-348), have demonstrated that it is possible to design or select a few members of this recognition alphabet. However, the specificity and affinity of these domains for their target DNA was rarely investigated in a rigorous and systematic fashion in these early studies.

Since Jacob and Monod questioned the chemical nature of the repressor and proposed a scheme by which the synthesis of individual proteins within a cell might be provoked or repressed, specific experimental control of gene expression has been a tantalizing prospect (Jacob, F. & Monod, J. (1961) J. Mol. Biol. 3, 318-356). It is now well established that genomes are regulated at the level of transcription primarily through the action of proteins known as transcription factors that bind DNA in a sequence specific fashion. Often these protein factors act in a complex combinatorial manner allowing temporal, spatial, and environmentally-responsive control of gene expression (Ptashne, M. (1997) Nature Medicine 3, 1069-1072). Transcription factors frequently act both through a DNA-binding domain which localizes the protein to a specific site within the genome, and through accessory effector domains which act to provoke (activate) or repress transcription at or near that site (Cowell, I. G. (1994) Trends Biochem. Sci. 19, 3842). Effector domains, such as the activation domain VP16 (Sadowski, I., Ma, J., Triezenberg, S. & Ptashne, M. (1988) Nature 335, 563-564) and the repression domain KRAB (Margolin, J. F., Friedman, J. R., Meyer, W., K.-H., Vissing, H., Thiesen, H.-J. & Rauscher III, F. J. (1994) Proc. Nat. Acad. Sci. USA 91, 4509-4513), are typically modular and retain their activity when they are fused to other DNA-binding proteins. Whereas genes might be readily controlled by directing transcription factors to particular sites within a genome, the design of DNA binding proteins that might be fashioned to bind any given sequence has been a daunting challenge. The present disclosure is based on the recognition of the structural features unique to the $Cys_2$-$His_2$ class of nucleic acid-binding, zinc finger proteins. The $Cys_2$-$His_2$ zinc finger domain consists of a simple Ada fold of approximately 30 amino acids in length. Structural stability of this fold is achieved by hydrophobic interactions and by chelation of a single zinc ion by the conserved $Cys_2$-$His_2$ residues (Lee, M. S., Gippert, G. P., Soman, K. V., Case, D. A. & Wright, P. E. (1989) Science 245, 635-637). Nucleic acid recognition is achieved through specific amino acid side chain contacts originating from the α-helix of the domain, which typically binds three base pairs of DNA sequence (Pavletich, N. P. & Pabo, C. O. (1991) Science 252, 809-17, Elrod-Erickson, M., Rould, M. A., Nekludova, L. & Pabo, C. O. (1996) Structure 4, 1171-1180). Unlike other nucleic acid recognition motifs, simple covalent linkage of multiple zinc finger domains allows the recognition of extended asymmetric sequences of DNA. Studies of natural zinc finger proteins have shown that three zinc finger domains can bind 9 bp of contiguous DNA sequence (Pavletich, N. P. & Pabo, C. O. (1991) Science 252, 809-17., Swirnoff, A. H. & Milbrandt, J. (1995) Mol. Cell. Biol. 15, 2275-87). Whereas recognition of 9 bp of sequence is insufficient to specify a unique site within even the small genome of *E. coli,* polydactyl proteins containing six zinc finger domains can specify 18-bp recognition (Liu, Q., Segal, D. J., Ghiara, J. B. & Barbas III, C. F. (1997) Proc. Natl. Acad. Sci. USA 94, 5525-5530). With respect to the development of a universal system for gene control, an 18-bp address can be sufficient to specify a single site within all known genomes. While polydactyl proteins of this type are unknown in nature, however, their efficacy in gene activation and repression within living human cells has recently been shown (Liu, Q., Segal, D. J., Ghiara, J. B. & Barbas III, C. F. (1997) Proc. Natl. Acad. Sci. USA 94, 5525-5530).

BRIEF SUMMARY OF THE INVENTION

In one aspect, the present invention provides an isolated and purified zinc finger-nucleotide binding polypeptide that contains the amino acid residue sequence of any of SEQ ID NO:1-16. In a related aspect, this invention further provides compositions comprising from two to about 12 such zinc finger-nucleotide binding polypeptides. The composition preferably contains from 2 to about 6 polypeptides. In a preferred embodiment, the zinc finger-nucleotide binding polypeptides are operatively linked, preferably by an amino acid residue linker having the sequence of SEQ ID NO 111. A composition of this invention specifically binds a nucleotide target that contains the sequence 5'-(GNN)$_n$-3', wherein each N is A, C, G, or T with the proviso that all N's cannot be C and where n is preferably 2 to 6. A polypeptide or composition can be further operatively linked to one or more transcription modulating factors such as a transcription activators or transcription suppressors or repressors. The present invention also provides an isolated and purified polynucleotide that encodes a polypeptide or composition of this invention and an expression vector containing such a polynucleotide.

In a still further aspect, the present invention provides a process of regulating the function of a nucleotide sequence that contains the sequence 5'-(GNN)$_n$-3', where n is an integer from 1 to 6, the process comprising exposing the nucleotide sequence to an effective amount of a composition of this invention operatively linked to one or more transcription modulating factors. The 5'-(GNN)$_n$-3' sequence can be found in the transcribed region or promoter region of the nucleotide or within an expressed sequence tag. In a preferred embodiment, the nucleotide sequence is part of an oncogene sequence. More preferably, the target nucleotide sequence is contained in a gene that encodes a member of an erbB receptor family. More preferably, the target nucleotide sequence is contained in an erbB gene. Preferred erbB genes are the human erbB-2 and erbB-3 genes.

The present disclosure demonstrates the simplicity and efficacy of a general strategy for the rapid production of gene switches. With a family of defined zinc finger domains recognizing sequences of the 5'-GNN-3' subset of a 64 member zinc finger alphabet, polydactyl proteins specifically recognizing novel 9- or, for the first time, 18-bp sequences were constructed and characterized. Potent transcription factors were generated and shown to control both gene activation and repression. Gene activation was achieved using the herpes simplex virus VP16 activation domain (Sadowski, I., Ma, J., Triezenberg, S. & Ptashne, M. (1988) Nature 335, 563-564) and a recombinant tetrameric repeat of its minimal activation domain. Gene repression or silencing was achieved using three effector domains of human origin, the kruppel associated box (KRAB) (Margolin, J. F., Friedman, J. R., Meyer, W., K.-H., Vissing, H., Thiesen, H.-J. & Rauscher III, F. J. (1994) Proc. Natl. Acad. Sci. USA 91, 45094513), the ERF repressor domain (ERD) (Sgouras, D. N., Athanasiou, M. A., Beal, G. J., Jr., Fisher, R. J., Blair, D. G. & Mavrothalassitis, G. J. (1995) EMBO J. 14, 4781-4793), and the mSIN3 interaction domain (SID) (Ayer, D. E., Laherty, C. D., Lawrence, Q. A., Armstrong, A. P. & Eisenman, R. N. (1996) Mol. Cell. Biol. 16, 5772-5781). Using luciferase reporter gene assays in human epithelial cells, the data show that artificial transcriptional regulators, designed to target the promoter of the proto-oncogene erbB-21HER-2, can ablate or activate gene expression in a specific manner. For the first time, gene activation or repression was achieved by targeting within the gene transcript, suggesting that information obtained from expressed sequence tags (ESTs) may be sufficient for the construction of gene switches. The novel methodology and materials described herein promise diverse applications in gene therapy, transgenic organisms, functional genomics, and other areas of cell and molecular biology.

BRIEF DESCRIPTION OF THE DRAWING

In the drawing, which forms a portion of the specification

FIG. 1 (shown in six panels) shows the binding specificity of regions of zinc finger-nucleotide binding polypeptides of the invention.

FIG. 2 shows (A) Alignment of E2C target sequence in the erbB-2 5'-UTR with the E3 target sequence in the erbB-3 5'-UTR. Numbers indicate the distance from the ATG translation initiation codon. (B) Amino acid sequence alignment of E2C and E3 proteins. DNA recognition helix sequence positions −1 to 6 of each finger, as well as sequence differences, are boxed.

DETAILED DESCRIPTION OF THE INVENTION

I. The Invention

The present invention provides zinc finger-nucleotide binding polypeptides, compositions containing one or more such polypeptides and the use of the polypeptides and compositions for modulating gene expression.

II. Compounds

A compound of this invention is an isolated zinc finger-nucleotide binding polypeptide that binds to a GNN nucleotide sequence and modulates the function of that nucleotide sequence. The polypeptide can enhance or suppress transcription of a gene, and can bind to DNA or RNA. A zinc finger-nucleotide binding polypeptide refers to a polypeptide which is a derivatized form of a wild-type zinc finger protein or one produced through recombination. A polypeptide may be a hybrid which contains zinc finger domain(s) from one protein linked to zinc finger domain(s) of a second protein, for example. The domains may be wild type or mutagenized. A polypeptide includes a truncated form of a wild type zinc finger protein. Examples of zinc finger proteins from which a polypeptide can be produced include TFIIIA and zif268.

A zinc finger-nucleotide binding polypeptide of this invention comprises a unique heptamer (contiguous sequence of 7 amino acid residues) within the α-helical domain of the polypeptide, which heptameric sequence determines binding specificity to a target necleotide. That heptameric sequence can be located anywhere within the α-helical domain but it is preferred that the heptamer extend from position −1 to position 6 as the residues are conventionally numbered in the art. A polypeptide of this invention can include any β-sheet and framework sequences known in the art to function as part of a zinc finger protein. A large number of zinc finger-nucleotide binding polypeptides were made and tested for binding specificity against target nucleotides containing a GNN triplet. The results of those studies are summarized in FIG. 1. In FIG. 1, the GNN triplet binding specificity for each peptide is shown in the right-hand column, with the highest specificity shown first and in boldface. In FIG. 1, SEQ ID Nos: are shown in parentheses. For each particular GNN (e.g., GAA, shown in the right-hand column of FIG. 1) target, the sequences are listed in order of decreasing specificity for that Triplet.

As shown in FIG. 1, the data show a striking conservation of all three of the primary DNA contact positions (−1, 3, and 6) was observed for virtually all the clones of a given target. Although many of these residues were observed previously at these positions following selections with much less complete libraries, the extent of conservation observed here represents a dramatic improvement over earlier studies (Choo, Y. & Klug, A. (1994) Proc Natl Acad Sci USA 91, 11163-7, Greisman, H. A. & Pabo, C. O. (1997) Science (Washington, D.C.) 275, 657-661, Rebar, E. J. & Pabo, C. O. (1994) Science (Washington, D.C., 1883-) 263, 671-3, Jamieson, A. C., Kim, S.-H. & Wells, J. A. (1994) Biochemistry 33, 5689-5695, Jamieson, A. C., Wang, H. & Kim, S.-H. (1996) PNAS 93, 12834-12839., Wu, H., Yang, W.-P. & Barbas III, C. F. (1995) PNAS 92, 344-348). The present invention discloses that the teachings of the prior art that the three helical positions −1, 3, and 6 of a zinc finger domain are sufficient to allow for the detailed description of the DNA binding specificity of the domain are incorrect.

Typically, phage selections have shown a consensus selection in only one or two of these positions. The greatest sequence variation occurred at the residues in positions 1 and 5, which do not make bases contacts in the Zif268/DNA structure and were expected not to contribute significantly to recognition (Pavietich, N. P. & Pabo, C. O. (1991) Science (Washington, D.C., 1883-) 252, 809-17, Elrod-Erickson, M., Rould, M. A., Nekludova, L. & Pabo, C. O. (1996) Structure (London) 4, 1171-1180). Variation in positions 1 and 5 also implied that the conservation in the other positions was due to their interaction with the DNA and not simply the fortuitous amplification of a single clone due to other reasons. Conservation of residue identity at position 2 was also observed. The conservation of position −2 is somewhat artifactual; the NNK library had this residue fixed as serine. This residue makes contacts with the DNA backbone in the Zif268 structure. Both libraries contained an invariant leucine at position 4, a critical residue in the hydrophobic core that stabilizes folding of this domain.

Impressive amino acid conservation was observed for recognition of the same nucleotide in different targets. For example, Asn in position 3 (Asn3) was virtually always selected to recognize adenine in the middle position, whether in the context of GAG, GM, GAT, or GAC. Gln-1 and Arg-1 were always selected to recognize adenine or guanine, respectively, in the 3' position regardless of context. Amide side chain based recognition of adenine by Gln or Asn is well documented in structural studies as is the Arg guanidinium side chain to guanine contact with a 3' or 5' guanine (Elrod-Erickson, M., Benson, T. E. & Pabo, C. O. (1998) Structure (London) 6, 451-464, Kim, C. A. & Berg, J. M. (1996) Nature Structural Biology 3, 940-945., Fairall, L., Schwabe, J. W. R., Chapman, L., Finch, J. T. & Rhodes, D. (1993) Nature (London) 366, 483-7). More often, however, two or three amino acids were selected for nucleotide recognition. His3 or Lys3 (and to a lesser extent, Gly3) were selected for the recognition of a middle guanine. Ser3 and Ala3 were selected to recognize a middle thymine. Thr3, Asp3, and Glu3 were selected to recognize a middle cytosine. Asp and Glu were also selected in position −1 to recognize a 3' cytosine, while Thr-1 and Ser-1 were selected to recognize a 3' thymine.

Selected Zif268 variants were subcloned into a bacterial expression vector, and the proteins overexpressed (finger-2 proteins, hereafter referred to by the subsite for which they were panned). It is important to study soluble proteins rather than phage-fusions since it is known that the two may differ significantly in their binding characteristics (Crameri, A., Cwirla, S. & Stemmer, W. P. (1996) Nat Med. 2, 100-102). The proteins were tested for their ability to recognize each of the 16 5'-GNN-3' finger-2 subsites using a multi-target ELISA assay. This assay provided an extremely rigorous test for specificity since there were always six "non-specific" sites which differed from the "specific" site by only a single nucleotide out of a nine-nucleotide target. Many of the phage-selected finger-2 proteins showed exquisite specificity, while others demonstrated varying degrees of crossreactivity. Some polypeptides actually bound better to subsites other than those for which they were selected.

Attempts were made to improve binding specificity by modifying the recognition helix using site-directed mutagenesis. Data from our selections and structural information guided mutant design. As the most exhaustive study performed to date, over 100 mutant proteins were characterized in an effort to expand our understanding of the rules of recognition. Although helix positions 1 and 5 are not expected to play a direct role in DNA recognition, the best improvements in specificity always involved modifications in these positions. These residues have been observed to make phosphate backbone contacts, which contribute to affinity in a non-sequence specific manner. Removal of non-specific contacts increases the importance of the specific contacts to the overall stability of the complex, thereby enhancing specificity. For example, the specificity of polypeptides for target triplets GAC, GAA, and GAG were improved simply by replacing atypical, charged residues in positions 1 and 5 with smaller, uncharged residues.

Another class of modifications involved changes to both binding and non-binding residues. The crossreactivity of polypeptides for GGG and the finger-2 subsite GAG was abolished by the modifications His3Lys and Thr5Val. It is interesting to note that His3 was unanimously selected during panning to recognize the middle guanine, although Lys3 provided better discrimination of A and G. This suggests that panning conditions for this protein may have favored selection by a parameter such as affinity over that of specificity. In the Zif268 structure, His3 donates a hydrogen bond to the N7 of the middle guanine (Pavletich, N. P. & Pabo, C. O. (1991) Science (Washington, D.C., 1883-) 252, 809-17, Elrod-Erickson, M., Rould, M. A., Nekludova, L. & Pabo, C. O. (1996) Structure (London) 4, 1171-1180). This bond could also be made with N7 of adenine, and in fact Zif268 does not discriminate between G and A in this position (Swirnoff, A. H. & Milbrandt, J. (1995) Mol. Cell. Biol. 15, 2275-87). His3 was found to specify only a middle guanine in polypeptides targeted to GGA, GGC, and GGT, even though Lys3 was selected during panning for GGC and GGT. Similarly, the multiple crossreactivities of polypeptides targeted to GTG were attenuated by modifications Lys1Ser and Ser3Glu, resulting in a 5-fold loss in affinity. Glu3 has been shown to be very specific for cytosine in binding site selection studies of Zif268 (Swirnoff, A. H. & Milbrandt, J. (1995) Mol. Cell. Biol. 15, 2275-87). No structural studies show an interaction of Glu3 with the middle thymine, and Glu3 was never selected to recognize a middle thymine in our study or any others (Choo, Y. & Klug, A. (1994) Proc Natl Acad Sci USA 91, 11163-7, Greisman, H. A. & Pabo, C. O. (1997) Science (Washington, D.C.) 275, 657-661, Rebar, E. J. & Pabo, C. O. (1994) Science (Washington, D.C., 1883-) 263, 671-3, Jamieson, A. C., Kim, S.-H. & Wells, J. A. (1994) Biochemistry 33, 5689-5695, Jamieson, A. C., Wang, H. & Kim, S.-H. (1996) PNAS 93,12834-12839, Isalan, M., Klug, A. & Choo, Y. (1998) Biochemistry 37,12026-33, Wu, H., Yang, W.-P. & Barbas III, C. F. (1995) PNAS 92, 344-348). Despite this, the Ser3Glu modification favored the recognition of a middle thymine over cytosine. These examples illustrate the limitations of relying on previous structures and selection data to understand the structural elements underlying specificity. It should also be emphasized that improvements by modifications involving positions 1 and 5 could not have been predicted by existing "recognition. codes" (Desjarlais, J. R. & Berg, J. M. (1992) Proc Natl Acad Sci USA 89, 7345-9. Suzuki, M., Gerstein, M. & Yagi, N. (1994) Nucleic Acids Res. 22, 3397-405, Choo, Y. & Klug, A. (1994) Proc. Natl. Acad. Sci. U.S.A. 91, 11168-72, Choo, Y. & Klug, A. (1997) Curr. Opin. Struct. Biol. 7, 117-125), which typically only consider positions −1, 2, 3, and 6. Only by the combination of selection and site-directed mutagenesis can we begin to fully understand the intricacies of zinc finger/DNA recognition.

From the combined selection and mutagenesis data it emerged that specific recognition of many nucleotides could be best accomplished using motifs, rather than a single amino acid. For example, the best specification of a 3' guanine was achieved using the combination of Arg-1, Ser1, and Asp2 (the RSD motif. By using Val5 and Arg6 to specify a 5' guanine, recognition of subsites GGG, GAG, GTG, and GCG could be accomplished using a common helix structure (SRSD-X-LVR) differing only in the position 3 residue (Lys3 for GGG, Asn3 for GAG, Glu3 for GTG, and Asp3 for GCG). Similarly, 3' thymine was specified using Thr-1, Ser1, and Gly2 in the final clones(the TSG motif). Further, a 3' cytosine could be specified using Asp-1, Pro1, and Gly2 (the DPG motif) except when the subsite was GCC; Pro1 was not tolerated by this subsite. Specification of a 3' adenine was with Gln-1, Ser1, Ser2 in two clones (QSS motif). Residues of positions 1 and 2 of the motifs were studied for each of the 3' bases and found to provide optimal specificity for a given 3' base as described here.

The multi-target ELISA assay assumed that all the proteins preferred guanine in the 5' position since all proteins contained Arg6 and this residue is known from structural studies to contact guanine at this position (Pavletich, N. P. & Pabo, C. O. (1991) Science (Washington, D.C., 1883-) 252, 809-17, Elrod-Erickson, M., Rould, M. A., Nekludova, L. & Pabo, C. O. (1996) Structure (London) 4, 1171-1180, Elrod-Erickson, M., Benson, T. E. & Pabo, C. O. (1998) Structure (London) 6, 451-464, Kim, C. A. & Berg, J. M. (1996) Nature Structural Biology 3, 940-945, Pavletich, N. P. & Pabo, C. O. (1993) Science (Washington, D.C., 1883-) 261,1701-7, Houbaviy, H. B., Usheva, A., Shenk, T. & Burley, S. K. (1996) Proc Nat Acad Sci USA 93,13577-82, Fairall, L., Schwabe, J. W. R., Chapman, L., Finch, J. T. & Rhodes, D. (1993) Nature (London) 366, 483-7, Wuttke, D. S., Foster, M. P., Case, D. A., Gottesfeld, J. M. & Wright, P. E. (1997) J. Mol. Biol. 273, 183-206, Nolte, R. T., Conlin, R. M., Harrison, S. C. & Brown, R. S. (1998) Proc. Natl. Acad. Sci. U.S.A. 95, 2938-2943). This interaction was demonstrated here using the 5' binding site signature assay ((Choo, Y. & Klug, A. (1994) Proc. Natl. Acad. Sci. U.S.A. 91, 11168-72); FIG. 2, white bars). Each protein was applied to pools of 16 oligonucleotide targets in which the 5' nucleotide of the finger-2 subsite was fixed as G, A, T, or C and the middle and 3' nucleotides were randomized. All proteins preferred the GNN pool with essentially no cross-reactivity.

The results of the multi-target ELISA assay were confirmed by affinity studies of purified proteins. In cases where crossreactivity was minimal in the ELISA assay, a single nucleotide mismatch typically resulted in a greater than 100-fold loss in affinity. This degree of specificity had yet to be demonstrated with zinc finger proteins. In general, proteins selected or designed to bind subsites with G or A in the middle and 3' position had the highest affinity, followed by those which had only one G or A in the middle or 3' position, followed by those which contained only T or C. The former group typically bound their targets with a higher affinity than Zif268 (10 nM), the latter with somewhat lower affinity, and almost all the proteins had an affinity lower than that of the parental C7 protein. There was no correlation between binding affinity and binding specificity suggesting that specificity can result not only from specific protein-DNA contacts, but also from interactions which exclude all but the correct nucleotide.

Asp2 was always co-selected with Arg-1 in all proteins for which the target subsite was GNG. It is now understood that there are two reasons for this. From structural studies of Zif268 (Pavletich, N. P. & Pabo, C. O. (1991) Science (Washington, D.C., 1883-) 252, 809-17, Elrod-Erickson, M., Rould, M. A., Nekludova, L. & Pabo, C. O. (1996) Structure (London) 4, 1171-1180), it is known that Asp2 of finger 2 makes a pair of buttressing hydrogen bonds with Arg-1 which stabilize the Arg-1/3' guanine interaction, as well as some water-mediated contacts. However, the carboxylate of Asp2 also accepts a hydrogen bond from the N4 of a cytosine that is base-paired to a 5' guanine of the finger-1 subsite. Adenine base paired to T in this position can make an analogous contact to that seen with cytosine. This interaction is particularly important because it extends the recognition subsite of finger 2 from three nucleotides (GNG) to four (GNG(G/T)) (Isalan, M., Choo, Y. & Klug, A. (1997) Proc. Nat. Acad. Sci. U.S.A. 94, 5617-5621., Jamieson, A. C., Wang, H. & Kim, S.-H. (1996) PNAS 93,12834-12839, Isalan, M., Klug, A. & Choo, Y. (1998) Biochemistry 37, 12026-33). This phenomenon is referred to as "target site overlap", and has three important ramifications. First, Asp2 was favored for selection by our library when the finger-2 subsite was GNG because our finger-1 subsite contained a 5' guanine. Second, it may limit the utility of the libraries used in this study to selection on GNN or TNN finger-2 subsites because finger 3 of these libraries contains an Asp2, which may help specify the 5' nucleotide of the finger-2 subsite to be G or T. In Zif268 and C7, which have Thr6 in finger 2, Asp2 of finger 3 enforces G or T recognition in the 5' position (T/G)GG. This interaction may also explain why previous phage display studies, which all used Zif268-based libraries, have found selection limited primarily to GNN recognition (Choo, Y. & Klug, A. (1994) Proc Natl Acad Sci USA 91, 11163-7., Rebar, E. J. & Pabo, C. O. (1994) Science (Washington, D.C., 1883-) 263, 671-3, Jamieson, A. C., Kim, S.-H. & Wells, J. A. (1994) Biochemistry 33, 5689-5695, Jamieson, A. C., Wang, H. & Kim, S.-H. (1996) PNAS 93, 12834-12839, Isalan, M., Klug, A. & Choo, Y. (1998) Biochemistry 37, 12026-33, Wu, H., Yang, W.-P. & Barbas III, C. F. (1995) PNAS 92, 344-348).

Finally, target site overlap potentially limits the use of these zinc fingers as modular building blocks. From structural data it is known that there are some zinc fingers in which target site overlap is quite extensive, such as those in GL1 and YY1, and others which are similar to Zif268 and display only modest overlap. In our final set of proteins, Asp2 is found in polypeptides that bind GGG, GAG, GTG, and GCG. The overlap potential of other residues found at position 2 is largely unknown, however structural studies reveal that many other residues found at this position may participate in such cross-subsite contacts. Fingers containing Asp2 may limit modularity, since they would require that each GNG subsite be followed by a T or G.

Table 1, below, summarized the sequences (SEQ ID NOs; 1-16) showing the highest selectivity for the sixteen embodiment of GNN target triplets.

TABLE 1

| Target Specificity | amino acids positions | | | | | | SEQ ID NO: |
|---|---|---|---|---|---|---|---|
| | -1 | 1 | 2 | 3 | 4 | 5 | 6 | |
| GAA | Q | S | S | N | L | V | R | 1 |
| GAC | D | P | G | N | L | V | R | 2 |
| GAG | R | S | D | N | L | V | R | 3 |
| GAT | T | S | G | N | L | V | R | 4 |
| GCA | Q | S | G | D | L | R | R | 5 |
| GCC | D | C | R | D | L | A | R | 6 |
| GCG | R | S | D | D | L | V | K | 7 |
| GCT | T | S | G | E | L | V | R | 8 |
| GGA | Q | R | A | H | L | E | R | 9 |
| GGC | D | P | G | H | L | V | R | 10 |
| GGG | R | S | D | K | L | V | R | 11 |
| GGT | T | S | G | H | L | V | R | 12 |
| GTA | Q | S | S | S | L | V | R | 13 |
| GTC | D | P | G | A | L | V | R | 14 |
| GTG | R | S | D | E | L | V | R | 15 |
| GTT | T | S | G | S | L | V | R | 16 |

The data show that all possible GNN triplet sequences can be recognized with exquisite specificity by zinc finger domains. Optimized zinc finger domains can discriminate single base differences by greater than 100-fold loss in affinity. While many of the amino acids found in the optimized proteins at the key contact positions -1, 3, and 6 are those that are consistent with a simple code of recognition, it has been discovered that optimal specific recognition is sensitive to the context in which these residues are presented. Residues at positions 1, 2, and 5 have been found to be critical for specific recognition. Further the data demonstrates for the first time that sequence motifs at positions -1, 1, and 2 rather than the simple identity of the position 1 residue are required for highly specific recognition of the 3' base. These residues likely provide the proper stereochemical context for interactions of the helix both in terms of recognition of specific bases and in the exclusion of other bases, the net result being highly specific interactions. Broad utility of these domains would be realized if they were modular in both their interactions with DNA and other zinc finger domains. This could be achieved by working within the likely limitations imposed by target site overlap, namely that sequences of the 5'-(GNN)$_n$-3' type should be targeted. Ready recombination of the disclosed domains then allows for the creation of polydactyl proteins of defined specificity precluding the need to develop phage display libraries in their generation. These polydactyl proteins have been used to activate and repress transcription driven by the human erbB-2 promoter in living cells. The family of zinc finger domains described herein is likely sufficient for the construction of $16^6$ or 17 million novel proteins that bind the 5'-(GNN)$_6$-3' family of DNA sequences.

The zinc finger-nucleotide binding polypeptide derivative can be derived or produced from a wild type zinc finger protein by truncation or expansion, or as a variant of the wild type-derived polypeptide by a process of site directed mutagenesis, or by a combination of the procedures. The term "truncated" refers to a zinc finger-nucleotide binding polypeptide that contains less that the full number of zinc fingers found in the native zinc finger binding protein or that has been deleted of non-desired sequences. For example, truncation of the zinc finger-nucleotide binding protein TFIIIA, which naturally contains nine zinc fingers, might be a polypeptide with only zinc fingers one through three. Expansion refers to a zinc finger polypeptide to which additional zinc finger modules have been added. For example, TFIIIA may be extended to 12 fingers by adding 3 zinc finger domains. In addition, a truncated zinc finger-nucleotide binding polypeptide may include zinc finger modules from more than one wild type polypeptide, thus resulting in a "hybrid" zinc finger-nucleotide binding polypeptide.

The term "mutagenized" refers to a zinc finger derived-nucleotide binding polypeptide that has been obtained by performing any of the known methods for accomplishing random or site-directed mutagenesis of the DNA encoding the protein. For instance, in TFIIIA, mutagenesis can be performed to replace nonconserved residues in one or more of the repeats of the consensus sequence. Truncated zinc finger-nucleotide binding proteins can also be mutagenized.

Examples of known zinc finger-nucleotide binding polypeptides that can be truncated, expanded, and/or mutagenized according to the present invention in order to inhibit the function of a nucleotide sequence containing a zinc finger-nucleotide binding motif includes TFIIIA and zif268. Other zinc finger-nucleotide binding proteins will be known to those of skill in the art.

A polypeptide of this invention can be made using a variety of standard techniques well known in the art (See, e.g., U.S. patent application Ser. No. 08/676,318, filed Jan. 18, 1995, the entire disclosure of which is incorporated herein by reference). Phage display libraries of zinc finger proteins were created and selected under conditions that favored enrichment of sequence specific proteins. Zinc finger domains recognizing a number of sequences required refinement by site-directed mutagenesis that was guided by both phage selection data and structural information.

The murine Cys$_2$-His$_2$ zinc finger protein Zif268 is used for construction of phage display libraries (Wu, H., Yang, W.-P. & Barbas III, C. F. (1995) PNAS 92, 344-348). Zif268 is structurally the most well characterized of the zinc-finger proteins (Pavletich, N. P. & Pabo, C. O. (1991) Science (Washington, D.C., 1883-) 252, 809-17, Elrod-Erickson, M., Rould, M. A., Nekludova, L. & Pabo, C. O. (1996) Structure (London) 4, 1171-1180, Swirnoff, A. H. & Milbrandt, J. (1995) Mol. Cell. Biol. 15, 2275-87). DNA recognition in each of the three zinc finger domains of this protein is mediated by residues in the N-terminus of the α-helix contacting primarily three nucleotides on a single strand of the DNA. The operator binding site for this three finger protein is 5'-GCGTGGGCG-3' (finger-2 subsite is underlined). Structural studies of Zif268 and other related zinc finger-DNA complexes (Elrod-Erickson, M., Benson, T. E. & Pabo, C. O. (1998) Structure (London) 6, 451-464, Kim, C. A. & Berg, J. M. (1996) Nature Structural Biology 3, 940-945, Pavletich, N. P. & Pabo, C. O. (1993) Science (Washington, D.C., 1883-) 261, 1701-7, Houbaviy, H. B., Usheva, A., Shenk, T. & Burley, S. K. (1996) Proc Natl Acad Sci USA 93, 13577-82, Fairall, L., Schwabe, J. W. R., Chapman, L., Finch, J. T. & Rhodes, D. (1993) Nature (London) 366, 483-7, Wuttke, D. S., Foster, M. P., Case, D. A., Gottesfeld, J. M. & Wright, P. E. (1997) J. Mol. Biol. 273, 183-206., Nolte, R. T., Conlin, R. M., Harrison, S. C. & Brown, R. S. (1998) Proc. Natl. Acad. Sci. U.S.A. 95, 2938-2943, Narayan, V. A., Kriwacki, R. W. & Caradonna, J. P. (1997) J. Biol. Chem. 272, 7801-7809) have shown that residues from primarily three positions on the α-helix, −1, 3, and 6, are involved in specific base contacts. Typically, the residue at position −1 of the α-helix contacts the 3' base of that finger's subsite while positions 3 and 6 contact the middle base and the 5' base, respectively.

In order to select a family of zinc finger domains recognizing the 5'-GNN-3' subset of sequences, two highly diverse zinc finger libraries were constructed in the phage display vector pComb3H (Barbas III, C. F., Kang, A. S., Lerner, R. A. & Benkovic, S. J. (1991) Proc. Natl. Acad. Sci. USA 88, 7978-7982., Rader, C. & Barbas III, C. F. (1997) Curr. Opin. Biotechnol. 8, 503-508). Both libraries involved randomization of residues within the .alpha.-helix of finger 2 of C7, a variant of Zif268 (Wu, H., Yang, W.-P. & Barbas III, C. F. (1995) PNAS 92, 344-348). Library 1 was constructed by randomization of positions −1,1,2,3,5,6 using a NNK doping strategy while library 2 was constructed using a VNS doping strategy with randomization of positions −2,−1,1,2,3,5,6. The NNK doping strategy allows for all amino acid combinations within 32 codons while VNS precludes Tyr, Phe, Cys and all stop codons in its 24 codon set. The libraries consisted of $4.4 \times 10^9$ and $3.5 \times 10^9$ members, respectively, each capable of recognizing sequences of the 5'-GCGNNNGCG-3' type. The size of the NNK library ensured that it could be surveyed with 99% confidence while the VNS library was highly diverse but somewhat incomplete. These libraries are, however, significantly larger than previously reported zinc finger libraries (Choo, Y. & Klug, A. (1994) Proc Natl Acad Sci USA 91, 11163-7, Greisman, H. A. & Pabo, C. O. (1997) Science (Washington, D.C.) 275,657-661, Rebar, E. J. & Pabo, C. O. (1994) Science (Washington, D.C., 1883-) 263, 671-3, Jamieson, A. C., Kim, S.-H. & Wells, J. A. (1994) Biochemistry 33, 5689-5695, Jamieson, A. C., Wang, H. & Kim, S.-H. (1996) PNAS 93, 12834-12839, Isalan, M., Klug, A. & Choo, Y. (1998) Biochemistry 37, 12026-33). Seven rounds of selection were performed on the zinc finger displaying-phage with each of the 16 5'-GCGGNNGCG-3' biotinylated hairpin DNAs targets using a solution binding protocol. Stringency was increased in each round by the addition of competitor DNA.

Sheared herring sperm DNA was provided for selection against phage that bound non-specifically to DNA. Stringent selective pressure for sequence specificity was obtained by providing DNAs of the 5'-GCGNNNGCG-3' types as specific competitors. Excess DNA of the 5'-GCGGNNGCG-3' type was added to provide even more stringent selection against binding to DNAs with single or double base changes as compared to the biotinylated target. Phage binding to the single biotinylated DNA target sequence were recovered using streptavidin coated beads. In some cases the selection process was repeated. The present data show that these domains are functionally modular and can be recombined with one another to create polydactyl proteins capable of binding 1 8-bp sequences with subnanomolar affinity. The family of zinc finger domains described herein is sufficient for the construction of 17 million novel proteins that bind the 5'-$(GNN)_6$-3' family of DNA sequences.

The invention includes a nucleotide sequence encoding a zinc finger-nucleotide binding polypeptide. DNA sequences encoding the zinc finger-nucleotide binding polypeptides of the invention, including native, truncated, and expanded polypeptides, can be obtained by several methods. For example, the DNA can be isolated using hybridization procedures which are well known in the art. These include, but are not limited to: (1) hybridization of probes to genomic or cDNA libraries to detect shared nucleotide sequences; (2) antibody screening of expression libraries to detect shared structural features; and (3) synthesis by the polymerase chain reaction (PCR). RNA sequences of the invention can be obtained by methods known in the art (See for example, Current Protocols in Molecular Biology Ausubel, et al. Eds., 1989).

The development of specific DNA sequences encoding zinc finger-nucleotide binding polypeptides of the invention can be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA is the least common. This is especially true when it is desirable to obtain the microbial expression of mammalian polypeptides due to the presence of introns.

For obtaining zinc finger derived-DNA binding polypeptides, the synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be clones. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucleic Acid Research 11:2325, 1983).

In another aspect, the present invention provides a pharmaceutical composition comprising a therapeutically effective amount of a zinc finger-nucleotide binding polypeptide or a therapeutically effective amount of a nucleotide sequence that encodes a zinc finger-nucleotide binding polypeptide in combination with a pharmaceutically acceptable carrier.

As used herein, the terms "pharmaceutically acceptable", "physiologically tolerable" and grammatical variations thereof, as they refer to compositions, carriers, diluents and reagents, are used interchangeable and represent that the materials are capable of administration to or upon a human without the production of undesirable physiological effects such as nausea, dizziness, gastric upset and the like which would be to a degree that would prohibit administration of the composition.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, as well as pH buffering agents and the like which enhance the effectiveness of the active ingredient.

The therapeutic pharmaceutical composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

III. Compositions

In another aspect, the present invention provides a plurality of zinc finger-nucleotide binding polypeptides operatively linked in such a manner to specifically bind a nucleotide target motif defined as 5'-(GNN)$_n$-3', where n is an integer greater than 1. Preferably, n is an integer from 2 to about 6.

Means for linking zinc finger-nucleotide binding polypeptide are described hereinafter in the Examples as well as in U.S. patent application Ser. No. 08/676,318 (filed Jan. 18, 1995). The individual polypeptides are preferably linked with oligopeptide linkers. Such linkers preferably resemble the linkers that are found in naturally occurring zinc finger proteins. A preferred linker for use in the present invention is the amino acid residue sequence TGEKP (SEQ ID NO:111).

To examine the efficacy of making such compositions and their use in gene control, the human erbB-2 and erbB-3 genes were chosen as a model. A polydactyl protein specifically recognizing an 18-bp sequence in the 5'-untranslated region of this gene was converted into a transcriptional repressor by fusion with KRAB, ERD, or SID repressor domains. Transcriptional activators were generated by fusion with the herpes simplex VP16 activation domain or with a tetrameric repeat of VP16's minimal activation domain, termed VP64. The data show for the first time that both gene repression and activation can be achieved by targeting designed proteins to a single site within the transcribed region of a gene.

The human erbB-2 and erbB-3 genes were chosen as model targets for the development of zinc finger-based transcriptional switches. Members of the ErbB receptor family play important roles in the development of human malignancies. In particular, erbB-2 is overexpressed as a result of gene amplification and/or transcriptional deregulation in a high percentage of human adenocarcinomas arising at numerous sites, including breast, ovary, lung, stomach, and salivary gland (Hynes, N. E. & Stern, D. F. (1994) Biochim. Biophys. Acta 1198,165-184). Increased expression of ErbB-2 leads to constitutive activation of its intrinsic tyrosine kinase, and has been shown to cause the transformation of cultured cells. Numerous clinical studies have shown that patients bearing tumors with elevated ErbB-2 expression levels have a poorer prognosis (Hynes, N. E. & Stern, D. F. (1994) Biochim. Biophys. Acta 1198, 165-184). In addition to its involvement in human cancer, erbB-2 plays important biological roles, both in the adult and during embryonal development of mammals (Hynes, N. E. & Stern, D. F. (1994) Biochim. Biophys. Acta 1198, 165-184, Altiok, N., Bessereau, J.-L. & Changeux, J.-P. (1995) EMBO J. 14, 42584266, Lee, K.-F., Simon, H., Chen, H., Bates, B., Hung, M.-C. & Hauser, C. (1995) Nature 378, 394-398).

The erbB-2 promoter therefore represents an interesting test case for the development of artificial transcriptional regulators. This promoter has been characterized in detail and has been shown to be relatively complex, containing both a TATA-dependent and a TATA-independent transcriptional initiation site (Ishii, S., Imamoto, F., Yamanashi, Y., Toyoshima, K. & Yamamoto, T. (1987) Proc. Natl. Acad. Sci. USA 84, 4374-4378). Whereas early studies showed that polydactyl proteins could act as transcriptional regulators that specifically activate or repress transcription, these proteins bound upstream of an artificial promoter to six tandem repeats of the proteins binding site (Liu, Q., Segal, D. J., Ghiara, J. B. & Barbas III, C. F. (1997) Proc. Natl. Acad. Sci. USA 94, 5525-5530). Furthermore, this study utilized polydactyl proteins that were not modified in their binding specificity. Herein, we tested the efficacy of polydactyl proteins assembled from predefined building blocks to bind a single site in the native erbB-2 promoter. Described above is the generation and characterization of a family of zinc finger domains that bind each of the 16 5'-GNN-3' DNA triplets. One reason we focused on the production of this family of recognition domains is that promoter regions of most organisms are relatively GC rich in their base content. Thus, if proteins recognizing 5'-(GNN)$_x$-3' sites could be readily assembled from this set of defined zinc finger domains, many genes could be rapidly and specifically targeted for regulation. A protein containing six zinc finger domains and recognizing 18 bp of DNA should be sufficient to define a single address within all known genomes. Examination of the erbB-2 promoter region revealed two 5'-(GNN)$_6$-3' sites and one 5'-(GNN)$_9$-3' site. One of these sites, identified here as e2c, falls within the 5'-untranslated region of the erbB-2 gene and was chosen as the target site for the generation of a gene-specific transcriptional switch. A BLAST sequence similarity search of the GenBank data base confirmed that this sequence is unique to erbB-2. The position of the e2c target sequence, downstream and in the vicinity of the two major transcription initiation sites, allowed for the examination of repression through inhibition of either transcription initiation or elongation. An interesting feature of the e2c target site is that it is found within a short stretch of sequence that is conserved between human, rat, and mouse erbB-2 genes (White, M. R.-A. & Hung, M.-C. (1992) Oncogene 7, 677-683). Thus, targeting of this site would allow for the study of this strategy in animal models prior to its application to human disease. For generating polydactyl proteins with desired DNA-binding specificity, the present studies have focused on the assembly of pre-defined zinc finger domains, which contrasts the sequential selection strategy proposed by Greisman and Pabo (Greisman, H. A. & Pabo, C. O. (1997) Science 275, 657-661). Such a strategy would require the sequential generation and selection of six zinc finger libraries for each required protein, making this experimental approach inaccessible to most laboratories and extremely time consuming to all. Further, since it is difficult to apply specific negative selection against binding alternative sequences in this strategy, proteins may result that are relatively unspecific as was recently reported (Kim, J.-S. & Pabo, C. O. (1997) J. Biol. Chem. 272, 29795-29800). The general utility of two different strategies for generating three-finger proteins recognizing 9 bp of DNA sequence was investigated. Each strategy was based on the modular nature of the zinc finger domain, and takes advantage of a family of zinc finger domains recognizing triplets of the 5'-GNN-3'. Two three-finger proteins recognizing halfsites (HS) 1 and 2 of the 5'-(GNN)$_6$-3' erbB-2 target site e2c were generated in the first strategy by fusing the pre-defined finger 2 (F2) domain variants together using a PCR assembly strategy. To examine the generality of this approach, three additional three-finger proteins recognizing sequences of the 5'-(GNN)$_3$-3' type, were prepared using the same approach. Purified zinc finger proteins were prepared as fusions with the maltose binding protein (MBP). ELISA analysis revealed that serially connected F2 proteins were able to act in concert to specifically recognize the desired 9-bp DNA target sequences. Each of the 5 proteins shown was able to discriminate between target and non-target 5'-(GNN).sub.3-3' sequence.

The affinity of each of the proteins for its target was determined by electrophoretic mobility-shift assays. These studies demonstrated that the zinc finger peptides have affinities comparable to Zif268 and other natural transcription factors with $K_d$ values that ranged from 3 to 70 nM. Here the $K_d$ of Zif268 for its operator to be 10 nM. It must be noted that, for reasons that remain to be explained, one group has reported $K_d$ values for the natural Zif268 protein that range from 6 nM to 10 pM, a 600-fold variation (Pavietich, N. P. & Pabo, C. O. (1991) Science 252, 809-17., Greisman, H. A. & Pabo, C. O. (1997) Science 275, 657-661). Most studies have reported the $K_d$ of the Zif268-DNA interaction to be from 3 to 10 nM, Choo, Y. & Klug, A. (1994) Proc. Natl. Acad. Sci. USA 91, 11163-11167, Hamilton, T. B., Borel, F. & Romaniuk, P. J. (1998) Biochemistry 37, 2051-2058). Thus, in order to compare the results reported here with those reported elsewhere, the relative $K_d$s should be compared, (Mutant $K_d$)/(Zif268 $K_d$), where both values are derived from the same report. The present data compare favorably to other studies of novel three-finger proteins prepared using phage display where affinities 10- to 200-fold weaker than Zif268 were reported (Greisman, H. A. & Pabo, C. O. (1997) Science 275, 657-661, Choo, Y., Sanchez-Garcia, I. & Klug, A. (1994) Nature 372, 642-5).

As an alternative to the serial connection of F2 domain variants, in the second strategy, three-finger proteins specific for the two e2c 5'-(GNN)$_3$-3' halfsites were produced by "helix grafting". The framework residues of the zinc finger domains, those residues that support the presentation of the recognition helix, vary between proteins. We anticipated that the framework residues may play a role in affinity and specificity. For helix grafting, amino acid positions –2 to 6 of the DNA recognition helices were either grafted into a Zif268 (Pavletich, N. P. & Pabo, C. O. (1991) Science 252, 809-17) or an Sp1C framework (Desjarlais, J. R. & Berg, J. M. (1993) Proc. Natl. Acad. Sci. USA 90, 2256-60). The Sp1C protein is a designed consensus protein shown to have enhanced stability towards chelating agents. The proteins were expressed from DNA templates prepared by a rapid PCR-based gene assembly strategy. In each case, ELISA analysis of MBP fusion proteins showed that the DNA binding specificities and affinities observed with the F2 framework constructs were retained.

As discussed above, the recognition of 9 bp of DNA sequence is not sufficient to specify a unique site within a complex genome. In contrast, a six-finger protein recognizing 18 bp of contiguous DNA sequence could define a single site in the human genome, thus fulfilling an important prerequisite for the generation of a gene-specific transcriptional switch. Six-finger proteins binding the erbB-2 target sequence e2c were generated from three-finger constructs by simple restriction enzyme digestion and cloning with F2, Zif268, and Sp1C framework template DNAs. ELISA analysis of purified MBP fusion proteins showed that each of the six-finger proteins was able to recognize the specific target sequence, with little cross reactivity to non-target 5'-(GNN)$_6$-3' sites or a tandem repeat of the Zif268 target site.

The affinity of each protein for the e2c DNA target site was determined by gel-shift analysis. A modest $K_d$ value of 25 nM was observed with the E2C(F2) six-finger protein constructed from the F2 framework, a value that is only 2 to 3 times better than its constituent three-finger proteins. In our previous studies of six-finger proteins, we observed approximately 70-fold enhanced affinity of the six-finger proteins for their DNA ligand as compared to their three-finger constituents (Liu, Q., Segal, D. J., Ghiara, J. B. & Barbas III, C. F. (1997) Proc. Natl. Acad. Sci. USA 94, 5525-5530). The absence of a substantial increase in the affinity of the E2C(F2) peptide suggested that serial connection of F2 domains is not optimal. It is possible that the periodicity of the F2 domains of the six-finger protein does not match that of the DNA over this extended sequence, and that a significant fraction of the binding energy of this protein is spent in unwinding DNA (Shi, Y. & Berg, J. M. (1996) Biochemistry 35, 3845-8). In contrast to the F2 domain protein, the E2C(Zif) and E2C(Sp1) six-finger proteins displayed 40- to 70-fold increased affinity as compared to their original three-finger protein constituents, with $K_d$ values of 1.6 nM and 0.5 nM, respectively. Significantly, both three-finger components of these proteins were involved in binding, since mutation of either half-site led to a roughly 100-fold decrease in affinity. The preponderance of known transcription factors bind their specific DNA ligands with nanomolar affinity, suggesting that the control of gene expression is governed by protein/DNA complexes of unexceptional life times. Thus, zinc finger proteins of increased affinity should not be required and could be disadvantageous, especially if binding to non-specific DNA is also increased.

The zinc finger domain is generally considered to be modular in nature, with each finger recognizing a 3-bp subsite (Pavletich, N. P. & Pabo, C. O. (1991) Science 252, 809-17). This is supported by our ability to recombine zinc finger domains in any desired sequence, yielding polydactyl proteins recognizing extended sequences of the structure 5'-(GNN)$_x$-3'. However, it should be noted that at least in some cases, zinc finger domains appear to specify overlapping 4 bp sites rather than individual 3 bp sites. In Zif268, residues in addition to those found at helix positions –1, 3, and 6 are involved in contacting DNA (Elrod-Erickson, M., Rould, M. A., Nekludova, L. & Pabo, C. O. (1996) Structure 4, 1171-1180). Specifically, an aspartate in helix position 2 of F2 plays several roles in recognition and makes a variety of contacts. The carboxylate of the aspartate side chain hydrogen bonds with arginine at position –1, stabilizing its interaction with the 3'-guanine of its target site. This aspartate also participates in water-mediated contacts with the guanine's complementary cytosine. In addition, this carboxylate is observed to make a direct contact to the N4 of the cytosine base on the opposite strand of the 5'-guanine base of the finger 1 binding site. It is this interaction which is the chemical basis for target site overlap. Indeed, when the Zif268 F2 libraries were selected against the four 5'-GCG GNG GCG-3' sequences, both an arginine at position –1 and an aspartate at position 2 were obtained, analogous to the residues in native Zif268. Since the e2c target sequence (5'-GGG GCC GGA GCC GCA GTG-3') (SEQ ID NO: 112) is followed by an A rather than a G, a potential target site overlap problem was anticipated with finger 1 of an e2c-specific six-finger protein. However, in both the Zif- and Sp1C-framework six-finger proteins, the GTG-specific finger 1 containing an aspartate at position 2 appears to recognize the sequences 5'-GTGA-3' and 5'-GTGG-3' equally well, as indicated by their very similar affinities to target sites e2c-a and e2c-g.

A polynucleotide or composition of this invention as set forth above, can be operatively linked to one or more transcription modulating factors. Modulating factors such as transcription activators or transcription suppressors or repressors are well known in the art. Means for operatively linking polypeptides to such factors are also well known in the art. Exemplary and preferred such factors and their use to modulate gene expression are discussed in detail hereinafter.

II Uses

In one embodiment, a method of the invention includes a process for modulating (inhibiting or suppressing) the function of a nucleotide sequence comprising a zinc finger-nucleotide binding motif which comprises contacting the zinc finger-nucleotide binding motif with an effective amount of a zinc finger-nucleotide binding polypeptide that binds to the motif. In the case where the nucleotide sequence is a promoter, the method includes inhibiting the transcriptional transactivation of a promoter containing a zinc finger-DNA binding motif. The term "inhibiting" refers to the suppression of the level of activation of transcription of a structural gene operably linked to a promoter, containing a zinc finger-nucleotide binding motif, for example. In addition, the zinc finger-nucleotide binding polypeptide derivative may bind a motif within a structural gene or within an RNA sequence.

The term "effective amount" includes that amount which results in the deactivation of a previously activated promoter or that amount which results in the inactivation of a promoter containing a zinc finger-nucleotide binding motif, or that amount which blocks transcription of a structural gene or translation of RNA. The amount of zinc finger derived-nucleotide binding polypeptide required is that amount necessary to either displace a native zinc finger-nucleotide binding protein in an existing protein/promoter complex, or that amount necessary to compete with the native zinc finger-nucleotide binding protein to form a complex with the promoter itself. Similarly, the amount required to block a structural gene or RNA is that amount which binds to and blocks RNA polymerase from reading through on the gene or that amount which inhibits translation, respectively. Preferably, the method is performed intracellularly. By functionally inactivating a promoter or structural gene, transcription or translation is suppressed. Delivery of an effective amount of the inhibitory protein for binding to or "contacting" the cellular nucleotide sequence containing the zinc finger-nucleotide binding protein motif, can be accomplished by one of the mechanisms described herein, such as by retroviral vectors or liposomes, or other methods well known in the art.

The term "modulating" refers to the suppression, enhancement or induction of a function. For example, the zinc finger-nucleotide binding polypeptide of the invention may modulate a promoter sequence by binding to a motif within the promoter, thereby enhancing or suppressing transcription of a gene operatively linked to the promoter nucleotide sequence. Alternatively, modulation may include inhibition of transcription of a gene where the zinc finger-nucleotide binding polypeptide binds to the structural gene and blocks DNA dependent RNA polymerase from reading through the gene, thus inhibiting transcription of the gene. The structural gene may be a normal cellular gene or an oncogene, for example. Alternatively, modulation may include inhibition of translation of a transcript.

The promoter region of a gene includes the regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA to RNA. In most cases the resulting RNA molecule serves as a template for synthesis of a specific protein; sometimes RNA itself is the final product.

The promoter region may be a normal cellular promoter or, for example, an onco-promoter. An onco-promoter is generally a virus-derived promoter. For example, the long terminal repeat (LTR) of retroviruses is a promoter region which may be a target for a zinc finger binding polypeptide variant of the invention. Promoters from members of the Lentivirusgroup, which include such pathogens as human T-cell lymphotrophic virus (HTLV) 1 and 2, or human immunodeficiency virus (HIV) 1 or 2, are examples of viral promoter regions which may be targeted for transcriptional modulation by a zinc finger binding polypeptide of the invention.

In order to test the concept of using zinc finger proteins as gene-specific transcriptional regulators, the E2C(Sp1) six-finger protein was fused to a number of effector domains. Transcriptional repressors were generated by attaching either of three human-derived repressor domains to the zinc finger protein. The first repressor protein was prepared using the ERF repressor domain (ERD) (Sgouras, D. N., Athanasiou, M. A., Beal, G. J., Jr., Fisher, R. J., Blair, D. G. & Mavrothalassitis, G. J. (1995) EMBO J. 14, 47814793), defined by amino acids 473 to 530 of the ets2 repressor factor (ERF). This domain mediates the antagonistic effect of ERF on the activity of transcription factors of the ets family. A synthetic repressor was constructed by fusion of this domain to the C-terminus of the zinc finger protein. The second repressor protein was prepared using the Kruppel-associated box (KRAB) domain (Margolin, J. F., Friedman, J. R., Meyer, W., K.-H., Vissing, H., Thiesen, H.-J. & Rauscher III, F. J. (1994) Proc. Natl. Acad. Sci. USA 91, 45094513). This repressor domain is commonly found at the N-terminus of zinc finger proteins and presumably exerts its repressive activity on TATA-dependent transcription in a distance- and orientation-independent manner (Pengue, G. & Lania, L. (1996) Proc. Natl. Acad. Sci. USA 93,1015-1020), by interacting with the RING finger protein KAP-1 (Friedman, J. R., Fredericks, W. J., Jensen, D. E., Speicher, D. W., Huang, X.-P., Neilson, E. G. & Rauscher III, F. J. (1996) Genes & Dev. 10, 2067-2078). We utilized the KRAB domain found between amino acids 1 and 97 of the zinc finger protein KOX1 (Margolin, J. F., Friedman, J. R., Meyer, W., K.-H., Vissing, H., Thiesen, H.-J. & Rauscher III, F. J. (1994) Proc. Natl. Acad. Sci. USA 91, 4509-4513). In this case an N-terminal fusion with the six-finger protein was constructed. Finally, to explore the utility of histone deacetylation for repression, amino acids 1 to 36 of the Mad mSIN3 interaction domain (SID) were fused to the N-terminus of the zinc finger protein (Ayer, D. E., Laherty, C. D., Lawrence, Q. A., Armstrong, A. P. & Eisenman, R. N. (1996) Mol. Cell. Biol. 16, 5772-5781). This small domain is found at the N-terminus of the transcription factor Mad and is responsible for mediating its transcriptional repression by interacting with mSIN3, which in turn interacts the co-repressor N-CoR and with the histone deacetylase mRPD1 (Heinzel, T., Lavinsky, R. M., Mullen, T.-M., Söderström, M., Laherty, C. D., Torchia, J., Yang, W.-M., Brard, G., Ngo, S. D. & al., e. (1997) Nature 387, 43-46). To examine gene-specific activation, transcriptional activators were generated by fusing the zinc finger protein to amino acids 413 to 489 of the herpes simplex virus VP16 protein (Sadowski, I., Ma, J., Triezenberg, S. & Ptashne, M. (1988) Nature 335, 563-564), or to an artificial tetrameric repeat of VP16's minimal activation domain, DALDDFDLDML (SEQ ID NO:113) (Seipel, K., Georgiev, O. & Schaffner, W. (1992) EMBO J. 11, 4961-4968), termed VP64.

Reporter constructs containing fragments of the erbB-2 promoter coupled to a luciferase reporter gene were generated to test the specific activities of our designed transcriptional regulators. The target reporter plasmid contained nucleotides −758 to −1 with respect to the ATG initiation codon, whereas the control reporter plasmid contained nucleotides −1571 to −24, thus lacking all but one nucleotide of the E2C binding site encompassed in positions −24 to −7. Both promoter fragments displayed similar activities when transfected transiently into HeLa cells, in agreement with previous observations (Hudson, L. G., Ertl, A. P. & Gill, G.

N. (1990) J. Biol. Chem. 265, 4389-4393). To test the effect of zinc finger-repressor domain fusion constructs on erbB-2 promoter activity, HeLa cells were transiently co-transfected with each of the zinc finger expression vectors and the luciferase reporter constructs. Significant repression was observed with each construct. The ERD and SID fusion proteins produced approximately 50% and 80% repression, respectively. The most potent repressor was the KRAB fusion protein. This protein caused complete repression of erbB-2 promoter activity. The observed residual activity was at the background level of the promoter-less pGL3 reporter. In contrast, none of the proteins caused significant repression of the control erbB-2 reporter construct lacking the E2C target site, demonstrating that repression is indeed mediated by specific binding of the E2C(Sp1) protein to its target site. Expression of a zinc finger protein lacking any effector domain resulted in weak repression, approximately 30%, indicating that most of the repression observed with the SID and KRAB constructs is caused by their effector domains, rather than by DNA-binding alone. This observation strongly suggests that the mechanism of repression is active inhibition of transcription initiation rather than of elongation. Once initiation of transcription by RNA polymerase II has occurred, the zinc finger protein appears to be readily displaced from the DNA by the action of the polymerase.

The utility of gene-specific polydactyl proteins to mediate activation of transcription was investigated using the same two reporter constructs. The VP16 fusion protein was found to stimulate transcription approximately 5-fold, whereas the VP64 fusion protein produced a 27-fold activation. This dramatic stimulation of promoter activity caused by a single VP16-based transcriptional activator is exceptional in view of the fact that the zinc finger protein binds in the transcribed region of the gene. This again demonstrates that mere binding of a zinc finger protein, even with one with sub-nanomolar affinity, in the path of RNA polymerase 11 need not necessarily negatively affect gene expression.

The data herein show that zinc finger proteins capable of binding novel 9- and 18-bp DNA target sites can be rapidly prepared using pre-defined domains recognizing 5'-GNN-3' sites. This information is sufficient for the preparation of $16^6$ or 17 million novel six-finger proteins each capable of binding 18 bp of DNA sequence. This rapid methodology for the construction of novel zinc finger proteins has advantages over the sequential generation and selection of zinc finger domains proposed by others (Greisman, H. A. & Pabo, C. O. (1997) Science 275, 657-661) and takes advantage of structural information that suggests that the potential for the target overlap problem as defined above might be avoided in proteins targeting 5'-GNN-3' sites. Using the complex and well studied erbB-2 promoter and live human cells, the data demonstrate that these proteins, when provided with the appropriate effector domain, can be used to provoke or activate expression and to produce graded levels of repression down to the level of the background in these experiments. These studies suggest that the KRAB domain is significantly more potent as a transcriptional repressor than ERD or SID domains, and that it is able to inhibit both the TATA-dependent and the TATA-independent transcriptional initiation of this promoter. These repressor domains have not previously been directly compared. The present strategy of using predefined zinc finger domains to construct polydactyl proteins coupled to effector domains has significant advantages over strategies that attempt to only repress transcription by competing or interfering with proteins involved in the transcription complex (Kim, J.-S. & Pabo, C. O. (1997) J. Biol. Chem. 272, 29795-29800, Kim, J.-S., Kim, J., Cepek, K. L., Sharp, P. A. & Pabo, C. O. (1997) Proc. Natl. Acad. Sci. USA 94, 3616-3620). Utilization of effector domains that have the potential to act over a distance should allow the application of these gene-switches to the regulation of uncharacterized genes and promoters. Since these transcriptional regulators might be prepared using our PCR-assembly strategy in a high-throughput fashion, we believe it is appropriate to comment on their potential practical applications. Novel DNA binding proteins generated in this manner should have potential utility in DNA-based diagnostic applications. For the study of gene function, we believe that the ability to both activate and repress the transcription of genes, at graded levels if necessary, may assist in assigning gene function. Since these proteins exert their control by acting in trans, functional gene knockout or activation might be produced in heterozygous transgenic animals. This would drastically reduce the time required to produce a gene knockout in a whole animal and would extend the range of organisms to which knockout technology might be applied. These proteins might also be used in gene therapy applications to inhibit the production of viral gene products or to activate genes involved in fighting disease. Significantly, the ease with which these proteins can be prepared will facilitate the testing of these ideas by the scientific community.

The Examples that follow illustrate preferred embodiments of the present invention and are not limiting of the specification or claims in any way.

EXAMPLE 1

Selection by Phage Display

Construction of zinc-finger libraries by PCR overlap extension was essentially as previously described (Shi, Y. & Berg, J. M. (1996) Biochemistry 35, 3845-8). Growth and precipitation of phage were as previously described (Pengue, G. & Lania, L. (1996) Proc. Natl. Acad. Sci. USA 93, 1015-1020, Friedman, J. R., Fredericks, W. J., Jensen, D. E., Speicher, D. W., Huang, X.-P., Neilson, E. G. & Rauscher III, F. J. (1996) Genes & Dev. 10, 2067-2078), except that ER2537 cells (New England Biolabs) were used to propagate the phage and 90 µM $ZnCl_2$ was added to the growth media. Precipitated phage were resuspended in Zinc Buffer A (ZBA; 10 mM Tris, pH7.5/90 mM KCl, 1 mM $MgCl_2$, 90 µM $ZnCl_2$)/1% BSA/5 mM DTT. Binding reactions (500 µl: ZBA/5 mM DTT/1% Blotto (BioRad)/competitor oligonucleotides/4 µg sheared herring sperm DNA (Sigma)/100 µl filtered phage ($\approx 10^{13}$ colony forming units)) were incubated for 30 minutes at room temperature, prior to the addition of 72 nM biotinylated hairpin target oligonucleotide. Incubation continued for 3.5 hours with constant gentle mixing. Streptavidin-coated magnetic beads (50 µp; Dynal) were washed twice with 500 ·mu·l ZBA/1% BSA, then blocked with 500 ·mu·l ZBA/5% Blotto/antibody-displaying (irrelevant) phage ($\approx 10^{12}$ colony forming units) for $\approx 4$ hours at room temperature. At the end of the binding period, the blocking solution was replaced by the binding reaction and incubated 1 hour at room temperature. The beads were washed 10 times over a 1 hour period with 500 µl ZBA/5 mM DTT/2% Tween 20, then once without Tween 20. Bound phage were eluted 30 minutes with 10 ·µg/µl trypsin.

Hairpin target oligonucleotides had the sequence 5'-Biotin-GGACGCN'N'N'CGCGGGTTTTCCCGCGNNN GCGTCC-3' (SEQ ID NO:114), where NNN was the 3-nucleotide finger 2-target sequence and N'N'N' its complement. A similar nonbiotinylated oligonucleotide, in which the target sequence was TGG (compTGG), was included at 7.2 nM in every round of selection to select against contaminating parental phage. Two pools of nonbiotinylated oligonucleotides were also used as competitors: one containing all 64 possible 3-nucleotide targets sequences (compNNN), the other containing all the GNN target sequences except for the current selection target (compGNN). These pools were typically used as follows: round 1, no compNNN or compGNN; round 2, 7.2 nM compGNN; round 3,10.8 nM compGNN; round 4,1.8 µM compNNN, 25 nM compGNN; round 5, 2.7 µM compNNN, 90 nM compGNN; round 6, 2.7 µM compNNN, 250 nM compGNN; round 7, 3.6 µM compNNN, 250 nM compGNN.

EXAMPLE 2

Multi-target Specificity Assays

The fragment of pComb3H (Pengue, G. & Lania, L. (1996) Proc. Natl. Acad. Sci. USA 93, 1015-1020, Heinzel, T., Lavinsky, R. M., Mullen, T.-M., Söderström, M., Laherty, C. D., Torchia, J., Yang, W.-M., Brard, G., Ngo, S. D. & al., e. (1997) Nature 387, 43-46) phagemid RF DNA containing the zinc-finger coding sequence was subcloned into a modified pMAL-c2 (New England Biolabs) bacterial expression vector and transformed into XL1-Blue (Stratagene). Freeze/thaw extracts containing the overexpressed maltose binding protein-zinc finger fusion proteins were prepared from IPTG-induced cultures using the Protein Fusion and Purification System (New England Biolabs). In 96-well ELISA plates, 0.2 µg of streptavidin (Pierce) was applied to each well for 1 hour at 37° C., then washed twice with water. Biotinylated target oligonucleotide (0.025 µg) was applied similarly. ZBA/3% BSA was applied for blocking, but the wells were not washed after incubation. All subsequent incubations were at room temperature. Eight 2-fold serial dilutions of the extracts were applied in 1×binding buffer (ZBA/1% BSA/5 mM DTT/0.12 µg/l sheared herring sperm DNA). The samples were incubated 1 hour, followed by 10 washes with water. Mouse anti-maltose binding protein mAb (Sigma) in ZBA/1% BSA was applied to the wells for 30 minutes, followed by 10 washes with water. Goat anti-mouse IgG mAb conjugated to alkaline phosphatase (Sigma) was applied to the wells for 30 minutes, followed by 10 washes with water. Alkaline phosphatase substrate (Sigma) was applied, and the $OD_{.405}$ was quantitated with SOFTmax 2.35 (Molecular Devices).

EXAMPLE 3

Gel Mobility Shift Assays

Fusion proteins were purified to >90% homogeneity using the Protein Fusion and Purification System (New England Biolabs), except that ZBA/5 mM DTT was used as the column buffer. Protein purity and concentration were determined from Coomassie blue-stained 15% SDS-PAGE gels by comparison to BSA standards. Target oligonucleotides were labeled at their 5' or 3' ends with [$^{32}$P] and gel purified. Eleven 3-fold serial dilutions of protein were incubated in 20 µl binding reactions (1×Binding Buffer/10% glycerol/≈1 pM target oligonucleotide) for three hours at room temperature, then resolved on a 5% polyacrlyamide gel in 0.5×TBE buffer. Quantitation of dried gels was performed using a PhosphorImager and ImageQuant software (Molecular Dynamics), and the $K_D$ was determined by Scatchard analysis.

EXAMPLE 4

Generation of Polydactyl Proteins with Desired DNA Binding Specificity

The studies reported here use the finger 2 (F2) variants pmGAC, pmGAG, pGCA, pGCC, pmGGA, pmGGC, pmGGG, and pGTG defined in the accompanying manuscript (Hudson, L. G., Ertl, A. P: & Gill, G. N. (1990) J. Biol. Chem. 265, 4389-4393). To generate DNAs encoding three-finger proteins, F2 coding regions were PCR amplified from selected or designed F2 variants and assembled by PCR overlap extension. Alternatively, DNAs encoding three-finger proteins with a Zif268 or Sp1C framework were synthesized from 8 or 6 overlapping oligonucleotides, respectively. Sp1C framework constructs, used for all reporter assays described in this report, were generated as follows. In the case of E2C-HS1(Sp1), 0.4 pmole each of oligonucleotides SPE2-3 (5'-GCG AGC MG GTC GCG GCA GTC ACT MA AGA TTT GCC GCA CTC TGG GCA TTT ATA CGG TTT TTC ACC-3') (SEQ ID NO:115) and SPE24 (5'-GTG ACT GCC GCG ACC TTG CTC GCC ATC MC GCA CTC ATA CTG GCG AGA AGC CAT ACA MT GTC CAG MT GTG GC-3') (SEQ ID NO:116) were mixed with 40 pmole each of oligonucleotides SPE2-2 (5'-GGT MG TCC TTC TCT CAG AGC TCT CAC CTG GTG CGC CAC CAG CGT ACC CAC ACG GGT GM MA CCG TAT MA TGC CCA GAG-3') (SEQ ID NO:117) and SPE2-5 (5'-ACG CAC CAG CTT GTC AGA GCG GCT GM AGA CTT GCC ACA TTC TGG ACA TTT GTA TGG C-3') (SEQ ID NO:118) in a standard PCR mixture and cycled 25 times (30 seconds at 94° C., 30 seconds at 60° C., 30 seconds at 72° C.). An aliquot of this pre-assembly reaction was then amplified with 40 pmole each of the primers SPE2-1 (5'-GAG GAG GAG GAG GTG GCC CAG GCG GCC CTC GAG CCC GGG GAG MG CCC TAT GCT TGT CCG GM TGT GGT MG TCC TTC TCT CAG AGC-3') (SEQ ID NO:119) and SPE2-6 (5'-GAG GAG GAG GAG CTG GCC GGC CTG GCC ACT AGT TTT TTT ACC GGT GTG AGT ACG TTG GTG ACG CAC CAG CTT GTC AGA GCG-3') (SEQ ID NO:120) using the same cycling conditions. The E2C-HS2(Sp1) DNA was generated in the same way, using an analogous set of oligonucleotides differing only in the recognition helix coding regions. All assembled three-finger coding regions were digested with the restriction endonuclease Sfi1 and cloned into pMal-CSS, a derivative of the bacterial expression vector pMal-C2 (New England Biolabs). DNAs encoding six-finger proteins with each of the different frameworks were assembled in pMal-CSS using Xma1 and BsrF1 restriction sites included in the sequences flanking the three-finger coding regions. Each of the zinc finger proteins was expressed in the *E coli* strain XL1-blue and binding properties were investigated by ELISA and gel shift analysis as described in the accompanying manuscript (Hudson, L. G., Ertl, A. P. & Gill, G. N. (1990) J. Biol. Chem. 265, 4389-4393).

EXAMPLE 5

Construction of Zinc Finger-effector Domain Fusion Proteins

For the construction of zinc finger-effector domain fusion proteins, DNAs encoding amino acids 473 to 530 of the ets repressor factor (ERF) repressor domain (ERD) (Sgouras, N., Athanasiou, M. A., Beal, G. J., Jr., Fisher, R. J., Blair, D. G. & Mavrothalassitis, G. J. (1995) EMBO J. 14, 4781-4793), amino acids 1 to 97 of the KRAB domain of KOX1

(Margolin, J. F., Friedman, J. R., Meyer, W., K.-H., Vissing, H., Thiesen, H.-J. & Rauscher III, F. J. (1994) Proc. Natl. Acad. Sci. USA 91, 45094513), or amino acids 1 to 36 of the Mad mSIN3 interaction domain (SID) (Ayer, D. E., Laherty, C. D., Lawrence, Q. A., Armstrong, A. P. & Eisenman, R. N. (1996) Mol. Cell. Biol. 16, 5772-5781) were assembled from overlapping oligonucleotides using Taq DNA polymerase. The coding region for amino acids 413 to 489 of the VP16 transcriptional activation domain (Sadowski, I., Ma, J., Triezenberg, S. & Ptashne, M. (1988) Nature 335, 563-564) was PCR amplified from pcDNA3/C7-C7-VP16 (10). The VP64 DNA, encoding a tetrameric repeat of VP16's minimal activation domain, comprising amino acids 437 to 447 (Seipel, K., Georgiev, O. & Schaffner, W. (1992) EMBO J. 11, 4961-4968), was generated from two pairs of complementary oligonucleotides. The resulting fragments were fused to zinc finger coding regions by standard cloning procedures, such that each resulting construct contained an internal SV40 nuclear localization signal, as well as a C-terminal HA decapeptide tag. Fusion constructs were cloned in the eucaryotic expression vector pcDNA3 (Invitrogen).

EXAMPLE 6

Construction of Luciferase Reporter Plasmids

An erbB-2 promoter fragment comprising nucleotides −758 to −1, relative to the ATG initiation codon, was PCR amplified from human bone marrow genomic DNA with the TaqExpand DNA polymerase mix (Boehringer Mannheim) and cloned into pGL3basic (Promega), upstream of the firefly luciferase gene. A human erbB-2 promoter fragment encompassing nucleotides −1571 to −24, was excised from pSVOAL.DELTA.5'/erbB-2(N-N) (Hudson, L. G., Ertl, A. P. & Gill, G. N. (1990) J. Biol. Chem. 265, 4389-4393) by Hind3 digestion and subcloned into pGL3basic, upstream of the firefly luciferase gene.

EXAMPLE 7

Luciferase Assays

For all transfections, HeLa cells were used at a confluency of 40-60%. Typically, cells were transfected with 400 ng reporter plasmid (pGL3-promoter constructs or, as negative control, pGL3basic), 50 ng effector plasmid (zinc finger constructs in pcDNA3 or, as negative control, empty pcDNA3), and 200 ng internal standard plasmid (phrAct-βGal) in a well of a 6 well dish using the lipofectamine reagent (Gibco BRL). Cell extracts were prepared approximately 48 hours after transfection. Luciferase activity was measured with luciferase assay reagent (Promega), βGal activity with Galacto-Light (Tropix), in a MicroLumat LB96P luminometer (EG&G Berthold). Luciferase activity was normalized on βGal activity.

EXAMPLE 8

Regulation of the erbB-2 Gene in Hela Cells

The erbB-2 gene was targeted for imposed regulation. The erbB-2 gene is frequently overexpressed in human cancers, particularly breast and ovarian, and elevated ErbB-2 levels correlate with a poor prognosis (N. E. Hynes and D. F. Stern, Biochim. Biophys. Acta 1198, 165 (1994)). To regulate the native erbB-2 gene, a synthetic repressor protein, designated E2C-KRAB, and a transactivator protein, designated E2C-VP64, were utilized (R. R. Beerli, D. J. Segal, B. Dreier, C. F. Barbas, III, Proc. Natl. Acad. Sci. USA 95, 14628 (1998)). Both proteins contain the same designed zinc finger protein E2C that recognizes the 18-bp DNA sequence 5'-GGG GCC GGA GCC GCA GTG-3' (SEQ ID NO:121) in the 5'-untranslated region of the proto-oncogene erbB-2. This DNA-binding protein was constructed from 6 pre-defined and modular zinc finger domains (D. J. Segal, B. Dreier, R. R. Beerli, C. F. Barbas, III, Proc. Natl. Acad. Sci. USA 96, 2758 (1999)). The repressor protein contains the Kox-1 KRAB domain (J. F. Margolin et al., Proc. Natl. Acad. Sci. USA 91, 4509 (1994)), whereas the transactivator VP64 contains a tetrameric repeat of the minimal activation domain (K. Seipel, O. Georgiev, W. Schaffner, EMBO J. 11, 4961 (1992)) derived from the herpes simplex virus protein VP16.

A derivative of the human cervical carcinoma cell line HeLa, HeLa/tet-off, was utilized (M. Gossen and H. Bujard, Proc. Natl. Acad. Sci. USA 89, 5547 (1992)). Since HeLa cells are of epithelial origin they express ErbB-2 and are well suited for studies of erbB-2 gene targeting. HeLa/tet-off cells produce the tetracycline-controlled transactivator, allowing induction of a gene of interest under the control of a tetracycline response element (TRE) by removal of tetracycline or its derivative doxycycline (Dox) from the growth medium. We have used this system to place our transcription factors under chemical control. Thus, the pRevTRE/E2C-SKD and pRevTRE/E2C-VP64 plasmids were constructed (The E2C(Sp1)-KRAB and E2C(Sp1)-VP64 coding regions were PCR amplified from pcDNA3-based expression plasmids (R. R. Beerli, D. J. Segal, B. Dreier, C. F. Barbas, III, Proc. Natl. Acad. Sci. USA 95, 14628 (1998)) and subcloned into pRevTRE (Clontech) using BamH1 and Cla1 restriction sites, and into pMX-IRES-GFP [X. Liu et al., Proc. Natl. Acad. Sci. USA 94, 10669 (1997)] using BamH1 and Not1 restriction sites. Fidelity of the PCR amplification was confirmed by sequencing), transfected into HeLa/tet-off cells, and 20 stable clones each were isolated and analyzed for Dox-dependent target gene regulation (The pRevTRE/E2C-KRAB and pRevTRE/E2C-VP64 constructs were transfected into the HeLa/tet-off cell line (M. Gossen and H. Bujard, Proc. Natl. Acad. Sci. USA 89, 5547 (1992)) using Lipofectamine Plus reagent (Gibco BRL). After two weeks of selection in hygromycin-containing medium, in the presence of 2 µg/ml Dox, stable clones were isolated and analyzed for Dox-dependent regulation of ErbB-2 expression. Western blots, immunoprecipitations, Northern blots, and flow cytometric analyses were carried out essentially as described [D. Graus-Porta, R. R. Beerli, N. E. Hynes, Mol. Cell. Biol. 15, 1182 (1995)].). As a read-out of erbB-2 promoter activity, ErbB-2 protein levels were initially analyzed by Western blotting. A significant fraction of these clones showed regulation of ErbB-2 expression upon removal of Dox for 4 days, i.e. downregulation of ErbB-2 in E2C-KRAB clones and upregulation in E2C-VP64 clones. ErbB-2 protein levels were correlated with altered levels of their specific mRNA, indicating that regulation of ErbB-2 expression was a result of repression or activation of transcription. The additional ErbB-2 protein expressed in E2C-VP64 clones was indistinguishable from naturally expressed protein and biologically active, since epidermal growth factor (EGF) readily induced its tyrosine phosphorylation. The ErbB-2 levels in the E2C-KRAB clone #27, in the absence of Dox, were below the level of detection as was its EGF-induced tyrosine phosphorylation. Therefore, ErbB-2 expression was also analyzed by flow cytometry, revealing no detectable ErbB-2 expression in E2C-KRAB clone #27, in sharp contrast to the dramatic upregulation (5.6 fold) of ErbB-2 in E2C-VP64 clone #18. Thus, the extent of erbB-2 gene regulation ranged from total repression (E2C-KRAB clone #27) to almost 6-fold activation (E2C-VP64 clone #18). No significant effect on the expression of the related ErbB-1 protein was observed, indicating that regulation of ErbB-2 expression was not a result of general down- or up-regulation of transcription. In contrast to the efficacy of these transcription factors that target 18 bps of DNA sequence using six zinc finger domains, transcriptional activators prepared with three zinc finger domains that bind either of the 9-bp half-sites of the E2C target sequence were unable to activate transcription of an erbB-2-luciferase reporter. These results suggest that the increased specificity and affinity of six finger proteins may be required to provide a dominant effect on gene regulation.

EXAMPLE 9

Introduction of the Coding Regions of the E2C-KRAB and E2C-VP64 Proteins into the Retroviral Vector pMX-IRES-GFP In order to express the E2C-KRAB and E2C-VP64 proteins in several other cell lines, their coding regions were introduced into the retroviral vector pMX-IRES-GFP. The E2C(Sp1)-KRAB and E2C(Sp1)-VP64 coding regions were PCR amplified from pcDNA3-based expression plasmids (R. R. Beerli, D. J. Segal, B. Dreier, C. F. Barbas, III, Proc. Natl. Acad. Sci. USA 95,14628 (1998)) and subcloned into pRevTRE (Clontech) using BamH1 and Cla1 restriction sites, and into pMX-IRES-GFP [X. Liu et al., Proc. Natl. Acad. Sci. USA 94, 10669 (1997)3 using BamH1 and Not1 restriction sites. Fidelity of the PCR amplification was confirmed by sequencing. This vector expresses a single bicistronic message for the translation of the zinc finger protein and, from an internal ribosome-entry site (IRES), the green fluorescent protein (GFP). Since both coding regions share the same mRNA, their expression is physically linked to one another and GFP expression is an indicator of zinc finger expression. Virus prepared from these plasmids was then used to infect the human carcinoma cell line A431 (pMX-IRES-GFP/E2C-KRAB and pMX-IRES-GFP/E2C-VP64 Plasmids were transiently transfected into the amphotropic packaging cell line Phoenix Ampho using Lipofectamine Plus (Gibco BRL) and, two days later, culture supernatants were used for infection of target cells in the presence of 8 µg/ml polybrene. Three days after infection, cells were harvested for analysis. Three days after infection, ErbB-2 expression was measured by flow cytometry. Significantly, about 59% of the E2C-KRAB virus treated cells were essentially ErbB-2 negative, while in about 27% of the E2C-VP64 virus treated cells ErbB-2 levels were increased. Plotting of GFP fluorescence vs. ErbB-2 fluorescence revealed that there were two cell populations, one with normal ErbB-2 levels that was GFP negative, and another with altered ErbB-2 levels that was GFP positive. Specificity of gene targeting was investigated by measuring the expression levels of the related ErbB-1 and ErbB-3 proteins. No significant alterations of these protein levels were detected, indicating that erbB-2 gene targeting is specific and not a non-specific result of general alterations in gene expression or overexpression of the effector domains. The lack of any appreciable regulation of erbB-3 is particularly remarkable since its 5'-UTR contains the 18bp sequence 5'-GGa GCC GGA GCC GgA GTc-3' (SEQ ID NO:122), that presents only 3 mismatches to E2C's designed target sequence (15 bp identity—lowercase letters indicate differences) (M. H. Kraus, W. Issing, T. Miki, N. C. Popescu, S. A. Aaronson, Proc. Natl. Acad. Sci. USA 86, 9193 (1989)).

EXAMPLE 10

Regulation of the erbB-2 Gene in Non-Human Primate Cells

The zinc finger target sequence within erbB-2's 5'-UTR lays within a 28-bp sequence stretch that is conserved in many species. To investigate regulation of erbB-2 gene expression in non-human primate cells, COS-7 fibroblasts were infected with the bicistronic E2C-KRAB retrovirus and analyzed by flow cytometry. As in human cells, expression of the repressor protein as indicated by the GFP marker correlated well with a loss of ErbB-2 protein. Similarly, gene targeting in murine cells was evaluated by infection of NIH/3T3 cells with E2C-KRAB and E2C-VP64 encoding retrovirus. ErbB-2 expression levels were then monitored by Western blotting rather than flow cytometry, due to a lack of reactivity of the mAb with the murine ErbB-2 extracellular domain. Here again, with E2C-KRAB a complete transcriptional knockout upon correction for infected cells was observed. However, unlike in human cell lines, E2C-VP64 induced ErbB-2 upregulation was rather modest in NIH/3T3 cells, approximately 1.8 fold upon correction for infection efficiency. A likely explanation for this discrepancy lies in the different structures of the human and mouse promoters. The mouse erbB-2 promoter, unlike the human, does not contain a TATA box (M. R. White and M. C. Hung, Oncogene 7, 677 (1992)). Transcriptional activation by VP16 is, at least in part, mediated by its interaction with TFIID, a multi-protein complex also containing the TATA-binding protein (C. J. Ingles, M. Shales, W. D. Cress, S. J. Triezenberg, J. Greenblatt, Nature 351, 588 (1991)). It is therefore plausible that the E2C-VP64 protein activates transcription less effectively in the absence of a TATA box. These data suggest that while a DNA binding site may be conserved with respect to sequence and relative position within a target cell, effector domains may need to be optimized for maximal efficiency due to context effects. Nevertheless, while their potencies may differ, the artificial transcription factors described here are capable of imposing regulation of erbB-2 gene transcription in cells derived from different species, providing a strategy for the study of gene function in a variety of organisms.

EXAMPLE 11

Specific Induction of G1 Accumulation of ErbB-2 Overexpressing Tumor Cells

Overexpression of ErbB-2 leads to constitutive activation of its intrinsic tyrosine kinase activity (P. P. Di Fiore et al., Science 237, 178 (1987)), and it has been shown that downregulation of ErbB-2 in tumor cells overexpressing the receptor leads to growth inhibition (R. M. Hudziak et al., Mol. Cell. Biol. 9, 1165 (1989); J. Deshane etal., Gene Ther. 1, 332 (1994); J. M. Daly et al., Cancer Res. 57, 3804 (1997)). The mechanism of growth inhibition appears to be that progression of the cells from the G1 to the S phase of the cell cycle is prevented (R. M. Neve, H. Sutterluty, N. Pullen, H. A. Lane, J. M. Daly, W. Krek, N. E. Hynes, Submitted for publication). Thus, we investigated if expression of our designed transcriptional repressor in erbB-2 overexpressing tumor cells would lead to a G1 block. Therefore, SKBR3 breast cancer cells were infected with E2C-KRAB retrovirus and cell-cycle distribution was analyzed in relation to ErbB-2 expression levels by flow cytometry (22). Two cell populations were observed: about 40% of the cells were not infected and had normal ErbB-2 levels, while the infected cells, .about.60%, displayed approximately 7-fold reduced receptor levels after 3 days. Compared to cells with normal receptor levels, a significantly larger fraction of cells with decreased ErbB-2 expression levels was in the G1 phase of the cell cycle. To ascertain that the G1 accumulation observed with SKBR3 cells was specific for ErbB-2 overexpressing tumor cells, a similar analysis was carried out with the T47D breast cancer cell line, which does not display elevated levels of ErbB-2 (FIG. 4B). Indeed, when T47D cells were infected with the E2C-KRAB retrovirus and subjected to flow cytometric analysis, cell populations with normal and reduced ErbB-2 levels were found to display indistinguishable DNA content. Thus, our designed repressor protein is able to specifically induce G1 accumulation of ErbB-2 overexpressing tumor cells. The ability to inhibit cell-cycle progression, and hence inhibit growth of ErbB-2 overexpressing tumor cells suggests the potential of designed transcription factors for cancer gene therapy.

EXAMPLE 12

Studies with erbB-3

Construction and Characterization of a Polydactyl Protein for Regulation of the erbB-3 Gene. Examination of the erbB-3 5'-UTR revealed the presence of an 18-bp sequence that was highly similar to the E2C target sequence in the erbB-2 5'-UTR (FIG. 2). Although they are at different distances and orientations with respect to the ATG initiation codons, the two sequences differ by only three nucleotides. Thus, a six-finger protein recognizing this sequence was made to investigate whether transcription factors could be designed to selectively regulate erbB-3 gene expression.

Described herein before are several strategies for the construction of polydactyl proteins from defined, modular building blocks. The most successful strategy involved grafting of the amino acid residues of each zinc finger involved in base-specific DNA recognition (a short α-helical region referred to as the "recognition helix") into the framework of the designed consensus protein Sp1C, a derivative of the transcription factor Sp1. Thus, the six-finger protein E3 designed to bind the 18-bp erbB-3 target sequence was built by using the Sp1C helix grafting strategy, the same method used for construction of the E2C protein described herein. An alignment of the E2C and E3 proteins reveals extensive sequence identity (FIG. 2). In particular, the entire protein framework, as well as three of the six recognition helices, are identical. Only the recognition helices of fingers 1, 2, and 6 were partially different, reflecting the fact that the 3-bp subsites recognized by these fingers differed by 1 nucleotide each.

For a detailed analysis of its binding properties, the E3 protein was purified as a fusion with the maltose-binding protein. Initially, an ELISA analysis was carried out, revealing specific binding of the E3 protein to its target site, with little or no crossreactivity to various other 5'-(GNN)$_6$-3' DNA sequences. A similar observation was made with the E2C protein. However, because of the similarity of the DNA sequences recognized, some crossreactivity of the two proteins with each other's target site was detected. To obtain a quantitative measure for the extent of discrimination between target and nontarget sequence, the affinities of the two proteins to each target sequence was determined by electrophoretic mobility-shift assay.

These studies revealed high-affinity binding of the E3 protein to its target, with a $K_d$ value of 0.35 nM (±10%), whereas the affinity of binding to the E2C target sequence was about 30-fold lower, with a $K_d$ value of 10 nM (±15%). Similarly, the affinity of the E2C protein to its target was subnanomolar, with a $K_d$ value of 0.75 nM (±15%), whereas binding to the E3 site was significantly weaker, with a $K_d$ value of 11 nM (±30%). Thus, both the E2C and the E3 proteins bind their respective target sequence with very high affinity and are able to discriminate between their cognate and very closely related DNA sequences.

Designed transcription factors were generated by fusing the E3 protein to repression or activation domains. In a manner analogous to the E2C fusion constructs, the E3-KRAB protein was produced by fusing the KRAB repressor domain to E3's N terminus, while E3-VP64 was generated by fusing the synthetic VP64 transactivation domain to its C terminus.

To analyze the ability of the erbB-3-specific transcription factors to impose a dominant regulatory effect on the native erbB-3 gene, the E3-KRAB and E3-VP64 coding regions were introduced into the retroviral vector pMX-IRES-GFP. Retroviruses prepared from this vector were then used to infect A431 cells. Three days after infection, expression levels of various members of the ErbB receptor family were monitored by flow cytometry.

Dramatic alterations in the levels of ErbB-3 were detected in significant fractions of infected cell populations. Expression was abolished in 74% of E3-KRAB virus-infected cells, whereas almost 8-fold higher ErbB-3 levels were detected in 48% of E3-VP64 virus-infected cells. Plotting of ErbB-3 fluorescence against GFP fluorescence revealed that only GFP-positive, i.e., infected, cells displayed altered ErbB-3 levels. Thus, E3-based transcription factors are as potent as E2C-based transcription factors in regulating target gene expression.

In contrast to the efficient regulation of ErbB-3 expression, neither E3-KRAB nor E3-VP64 affected ErbB-1 and ErbB-2 expression levels. Given the similarity of the E3 and E2C target sequences, the lack of a significant effect on erbB-2 gene expression is yet another demonstration of the exquisite specificity inherent to the zinc finger-based gene switches described here.

What is claimed is:

1. An isolated and purified zinc finger-nucleotide binding polypeptide that contains from 2 to 6 nucleotide binding regions, said nucleotide binding regions selected from the group consisting of the amino acid sequences SEQ ID NO: 42 and SEQ ID NO: 107, wherein at least one nucleotide binding region comprises the amino acid sequence SEQ ID NO: 42.

2. An isolated and purified zinc finger-nucleotide binding polypeptide that contains from 2 to 6 nucleotide binding regions, wherein said zinc finger-nucleotide binding polypeptide comprises the nucleotide binding region having the amino acid sequence SEQ ID NO: 42.

3. A composition comprising the zinc finger-nucleotide binding polypeptide of claim 1.

4. A composition comprising the zinc finger-nucleotide binding polypeptide of claim 2.

5. An isolated and purified polynucleotide encoding a zinc finger-nucleotide binding polypeptide that contains from 2 to 6 nucleotide binding regions, said nucleotide binding regions selected from the group consisting of the amino acid sequences SEQ ID NO: 42 and SEQ ID NO: 107, wherein at least one nucleotide binding region comprises the amino acid sequence SEQ ID NO: 42.

6. An isolated and purified polynucleotide encoding a zinc finger-nucleotide binding polypeptide that contains from 2 to 6 nucleotide binding regions, wherein said zinc finger-nucleotide binding polypeptide comprises the nucleotide binding region having the amino acid sequence SEQ ID NO: 42.

7. An expression vector comprising the polynucleotide of claim 5.

8. An expression vector comprising the polynucleotide of claim 6.

9. A process of regulating a nucleotide sequence that contains the sequence 5'-(GNN)$_n$-3', where n is an integer from 1 to 6, the process comprising exposing the nucleotide sequence to an effective amount of the composition of claim 3.

10. A process of regulating a nucleotide sequence that contains the sequence 5'-(GNN)$_n$-3', where n is an integer from 1 to 6, the process comprising exposing the nucleotide sequence to an effective amount of the composition of claim 4.

11. The process of claim 9 wherein the sequence 5'-(GNN)$_n$-3' is located in the transcribed region of the nucleotide sequence.

12. The process of claim 10 wherein the sequence 5'-(GNN)$_n$-3' is located in the transcribed region of the nucleotide sequence.

13. The process of claim 9 wherein the sequence 5'-(GNN)$_n$-3' is located in a promoter region of the nucleotide sequence.

14. The process of claim 10 wherein the sequence 5'-(GNN)$_n$-3' is located in a promoter region of the nucleotide sequence.

15. The process of claim 9 wherein the sequence 5'-(GNN)$_n$-3' is located in an expressed sequence tag.

16. The process of claim 10 wherein the sequence 5'-(GNN)$_n$-3' is located in an expressed sequence tag.

17. The process of claim 9 wherein the composition is operatively linked to one or more transcription modulating factors.

18. The process of claim 10 wherein the composition is operatively linked to one or more transcription modulating factors.

* * * * *

SEQUENCE LISTING

<160> NUMBER OF SEQ ID NOS: 129

<210> SEQ ID NO 1
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Gln Ser Ser Asn Leu Val Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Pro Gly Asn Leu Val Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Asn Leu Val Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Ser Gly Asn Leu Val Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Gly Asp Leu Arg Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Cys Arg Asp Leu Ala Arg
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp Asp Leu Val Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ser Gly Glu Leu Val Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Arg Ala His Leu Glu Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Pro Gly His Leu Val Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Lys Leu Val Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 12

Thr Ser Gly His Leu Val Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ser Ser Leu Val Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Pro Gly Ala Leu Val Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Asp Glu Leu Val Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Gly Ser Leu Val Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Ser Asn Leu Val Arg
1               5

<210> SEQ ID NO 18
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 18

Gln Ser Gly Asn Leu Val Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Pro Gly Asn Leu Val Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Pro Gly Asn Leu Lys Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Asn Leu Arg Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ser Ala Asn Leu Val Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Asn Leu Val Lys
1               5
```

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Ser Ala Gln Leu Val Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Ser Thr Leu Val Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Gly Thr Leu Arg Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Pro Gly Asp Leu Val Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gly Pro Asp Leu Val Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 29

Gln Ala Gly Thr Leu Met Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Pro Gly Thr Leu Val Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gly Pro Glu Leu Val Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Cys Arg Glu Leu Ser Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Pro Ser Thr Leu Lys Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Pro Ser Asp Leu Lys Arg
1               5

<210> SEQ ID NO 35
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ser Gly Asp Leu Val Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Ser Gly Glu Leu Val Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Ser Gly Glu Leu Lys Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Leu Asp Thr Leu Gly Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Pro Gly Asp Leu Val Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Asp Thr Leu Val Arg
```

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Lys Ser Ala Asp Leu Lys Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Arg Ser Asp Asp Leu Val Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Arg Ser Asp Thr Leu Val Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Lys Ser Ala Glu Leu Lys Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Lys Ser Ala Glu Leu Val Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 46

Arg Gly Pro Glu Leu Val Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Pro Gly Glu Leu Val Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Ser Gln Thr Leu Thr Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Pro Gly Glu Leu Val Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ser Gly Asp Leu Val Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ser Gln Thr Leu Val Arg
1               5

<210> SEQ ID NO 52
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ser Gln Thr Leu Thr Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Gly Glu Leu Lys Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Ser Ser Asp Leu Val Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ser Gly Thr Leu Val Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Pro Gly Thr Leu Val Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57
```

```
Thr Ser Gln Asp Leu Lys Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Ser Gly Thr Leu Val Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ser Ser His Leu Val Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ser Gly His Leu Val Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Pro Gly His Leu Val Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Arg Ser Lys Leu Ala Arg
1               5

<210> SEQ ID NO 63
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 63

Asp Pro Gly His Leu Ala Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Arg Ala Lys Leu Glu Arg
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ser Ser Lys Leu Val Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Arg Ser Lys Leu Ala Arg
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Pro Gly Lys Leu Ala Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ser Asp Lys Leu Thr Arg
1               5
```

```
<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ser Asp His Leu Thr Arg
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Ser Ala Lys Leu Glu Arg
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ala Asp His Leu Ser Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ala Asp Lys Leu Ser Arg
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Pro Gly His Leu Val Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Thr Ser Ser His Leu Val Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Ser Gly Lys Leu Val Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Pro Gly Glu Leu Val Arg
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ser Gly Glu Leu Val Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Ser Gly Glu Leu Arg Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Pro Gly Ser Leu Val Arg
1               5

<210> SEQ ID NO 80
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 80

Arg Lys Asp Ser Leu Val Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ser Asp Val Leu Val Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg His Asp Ser Leu Leu Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ser Asp Ala Leu Val Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ser Ser Ser Leu Val Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Ser Ser His Val Arg
1               5
```

```
<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ser Asp Glu Leu Val Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ser Asp Ala Leu Val Lys
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ser Asp Val Leu Val Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser Ser Ala Leu Val Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Lys Asp Ser Leu Val Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 91

Arg Ser Ala Ser Leu Val Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Ser Asp Ser Leu Val Arg
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ile His Ser Leu Val Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Pro Gly Ser Leu Val Arg
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Gly Pro Ser Leu Val Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Pro Gly Ala Leu Val Arg
1               5

<210> SEQ ID NO 97
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 97

Lys Ser Ala Ser Leu Val Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Ser Ala Ala Leu Val Arg
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Ser Ala Val Leu Val Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Ser Gly Ser Leu Thr Arg
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Ser Gln Ser Leu Val Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Ser Ser Ser Leu Val Arg
1               5
```

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Pro Gly Ser Leu Val Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Ser Gly Ala Leu Val Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Pro Gly Ala Leu Val Arg
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Gly Gly Ser Leu Val Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Ser Gly Glu Leu Val Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Ser Gly Glu Leu Thr Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Thr Ser Ser Ala Leu Val Lys
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Ser Ser Ala Leu Val Arg
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Gly Glu Lys Pro
1               5

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggggccggag ccgcagtg                                                 18

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ala Leu Asp Asp Phe Asp Leu Asp Met Leu
1               5                   10

<210> SEQ ID NO 114
<211> LENGTH: 34
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(9)
<223> OTHER INFORMATION: a, c, g, or t
<220> FEATURE:
<221> NAME/KEY: modified_base
<222> LOCATION: (26)..(28)
<223> OTHER INFORMATION: a, c, g, or t

<400> SEQUENCE: 114
ggacgcnnnc gcgggttttc ccgcgnnngc gtcc                                34

<210> SEQ ID NO 115
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
gcgagcaagg tcgcggcagt cactaaaaga tttgccgcac tctgggcatt tatacggttt    60
ttcacc                                                               66

<210> SEQ ID NO 116
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
gtgactgccg cgaccttgct cgccatcaac gcactcatac tggcgagaag ccatacaaat    60
gtccagaatg tggc                                                      74

<210> SEQ ID NO 117
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
ggtaagtcct tctctcagag ctctcacctg gtgcgccacc agcgtaccca cacgggtgaa    60
aaaccgtata aatgcccaga g                                              81

<210> SEQ ID NO 118
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
acgcaccagc ttgtcagagc ggctgaaaga cttgccacat tctggacatt tgtatggc      58

<210> SEQ ID NO 119
<211> LENGTH: 87
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 119
gaggaggagg aggtggccca ggcggccctc gagcccgggg agaagcccta tgcttgtccg    60
gaatgtggta agtccttctc tcagagc                                       87

<210> SEQ ID NO 120
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gaggaggagg agctggccgg cctggccact agttttttta ccggtgtgag tacgttggtg    60
acgcaccagc ttgtcagagc g                                             81

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggggccggag ccgcagtg                                                 18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ggagccggag ccggagtc                                                 18

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
agccatgggg ccggagccgc agtgagcacc                                    30

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gcaatcggag ccggagccgg agtccgggga                                    30

-continued

<210> SEQ ID NO 125
<211> LENGTH: 185
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 125

Met Ala Gln Ala Ala Leu Glu Pro Gly Glu Lys Pro Tyr Ala Cys Pro
1               5                   10                  15

Glu Cys Gly Lys Ser Phe Ser Arg Lys Asp Ser Leu Val Arg His Gln
            20                  25                  30

Arg Thr His Thr Gly Glu Lys Pro Tyr Lys Cys Pro Glu Cys Gly Lys
        35                  40                  45

Ser Phe Ser Gln Ser Gly Asp Leu Arg Arg His Gln Arg Thr His Thr
    50                  55                  60

Gly Glu Lys Pro Tyr Lys Cys Pro Glu Cys Gly Lys Ser Phe Ser Asp
65                  70                  75                  80

Cys Arg Asp Leu Ala Arg His Gln Arg Thr His Thr Gly Glu Lys Pro
                85                  90                  95

Tyr Ala Cys Pro Glu Cys Gly Lys Ser Phe Ser Gln Ser Ser His Leu
            100                 105                 110

Val Arg His Gln Arg Thr His Thr Gly Glu Lys Pro Tyr Lys Cys Pro
        115                 120                 125

Glu Cys Gly Lys Ser Phe Ser Asp Gly Arg Asp Leu Ala Arg His Gln
    130                 135                 140

Arg Thr His Thr Gly Glu Lys Pro Tyr Lys Cys Pro Glu Cys Gly Lys
145                 150                 155                 160

Ser Phe Ser Arg Ser Asp Lys Leu Val Arg His Gln Arg Thr His Thr
                165                 170                 175

Gly Lys Lys Thr Ser Gly Gln Ala Gly
            180                 185

<210> SEQ ID NO 126
<211> LENGTH: 185
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 126

Met Ala Gln Ala Ala Leu Glu Pro Gly Glu Lys Pro Tyr Ala Cys Pro
1               5                   10                  15

Glu Cys Gly Lys Ser Phe Ser Asp Pro Gly Ala Leu Val Arg His Gln
            20                  25                  30

Arg Thr His Thr Gly Glu Lys Pro Tyr Lys Cys Pro Glu Cys Gly Lys
        35                  40                  45

Ser Phe Ser Gln Ser Ser His Leu Val Arg His Gln Arg Thr His Thr
    50                  55                  60

Gly Glu Lys Pro Tyr Lys Cys Pro Glu Cys Gly Lys Ser Phe Ser Asp
65                  70                  75                  80

Cys Arg Asp Leu Ala Arg His Gln Arg Thr His Thr Gly Glu Lys Pro
                85                  90                  95

Tyr Ala Cys Pro Glu Cys Gly Lys Ser Phe Ser Gln Ser Ser His Leu
            100                 105                 110

Val Arg His Gln Arg Thr His Thr Gly Glu Lys Pro Tyr Lys Cys Pro

```
                   115                 120                 125

Glu Cys Gly Lys Ser Phe Ser Asp Cys Arg Asp Leu Ala Arg His Gln
    130                 135                 140

Arg Thr His Thr Gly Glu Lys Pro Tyr Lys Cys Pro Glu Cys Gly Lys
145                 150                 155                 160

Ser Phe Ser Gln Ser Ser His Leu Val Arg His Gln Arg Thr His Thr
                165                 170                 175

Gly Lys Lys Thr Ser Gly Gln Ala Gly
            180                 185

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, c, g, or t
<220> FEATURE:
<221> NAME/KEY: modified_base
<222> LOCATION: (5)..(6)
<223> OTHER INFORMATION: a, c, g, or t
<220> FEATURE:
<221> NAME/KEY: modified_base
<222> LOCATION: (8)..(9)
<223> OTHER INFORMATION: a, c, g, or t
<220> FEATURE:
<221> NAME/KEY: modified_base
<222> LOCATION: (11)..(12)
<223> OTHER INFORMATION: a, c, g, or t
<220> FEATURE:
<221> NAME/KEY: modified_base
<222> LOCATION: (14)..(15)
<223> OTHER INFORMATION: a, c, g, or t
<220> FEATURE:
<221> NAME/KEY: modified_base
<222> LOCATION: (17)..(18)
<223> OTHER INFORMATION: a, c, g, or t
<220> FEATURE:
<223> OTHER INFORMATION: This sequence may encompass 1 to 6 repeats of
      the gnn nucleotide motif

<400> SEQUENCE: 127
gnngnngnng nngnngnn                                                    18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, c, g, or t
<220> FEATURE:
<221> NAME/KEY: modified_base
<222> LOCATION: (5)..(6)
<223> OTHER INFORMATION: a, c, g, or t
<220> FEATURE:
<221> NAME/KEY: modified_base
<222> LOCATION: (8)..(9)
<223> OTHER INFORMATION: a, c, g, or t
<220> FEATURE:
<221> NAME/KEY: modified_base
<222> LOCATION: (11)..(12)
<223> OTHER INFORMATION: a, c, g, or t
<220> FEATURE:
```

```
-continued

<221> NAME/KEY: modified_base
<222> LOCATION: (14)..(15)
<223> OTHER INFORMATION: a, c, g, or t
<220> FEATURE:
<221> NAME/KEY: modified_base
<222> LOCATION: (17)..(18)
<223> OTHER INFORMATION: a, c, g, or t

<400> SEQUENCE: 128
gnngnngnng nngnngnn                                              18

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: a, c, g, or t
<220> FEATURE:
<221> NAME/KEY: modified_base
<222> LOCATION: (5)..(6)
<223> OTHER INFORMATION: a, c, g, or t
<220> FEATURE:
<221> NAME/KEY: modified_base
<222> LOCATION: (8)..(9)
<223> OTHER INFORMATION: a, c, g, or t
<220> FEATURE:
<221> NAME/KEY: modified_base
<222> LOCATION: (11)..(12)
<223> OTHER INFORMATION: a, c, g, or t
<220> FEATURE:
<221> NAME/KEY: modified_base
<222> LOCATION: (14)..(15)
<223> OTHER INFORMATION: a, c, g, or t
<220> FEATURE:
<221> NAME/KEY: modified_base
<222> LOCATION: (17)..(18)
<223> OTHER INFORMATION: a, c, g, or t
<220> FEATURE:
<221> NAME/KEY: modified_base
<222> LOCATION: (20)..(21)
<223> OTHER INFORMATION: a, c, g, or t
<220> FEATURE:
<221> NAME/KEY: modified_base
<222> LOCATION: (23)..(24)
<223> OTHER INFORMATION: a, c, g, or t
<220> FEATURE:
<221> NAME/KEY: modified_base
<222> LOCATION: (26)..(27)
<223> OTHER INFORMATION: a, c, g, or t

<400> SEQUENCE: 129
gnngnngnng nngnngnngn ngnngnn                                    27
```